(12) United States Patent
Taub et al.

(10) Patent No.: US 12,426,812 B2
(45) Date of Patent: *Sep. 30, 2025

(54) ANALYTE MONITORING AND MANAGEMENT DEVICE AND METHOD TO ANALYZE THE FREQUENCY OF USER INTERACTION WITH THE DEVICE

(71) Applicant: ABBOTT DIABETES CARE INC., Alameda, CA (US)

(72) Inventors: Marc Barry Taub, Mountain View, CA (US); Jolyon Robert Bugler, Combe (GB); Thomas A. Peyser, Menlo Park, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/666,331

(22) Filed: May 16, 2024

(65) Prior Publication Data

US 2024/0298933 A1    Sep. 12, 2024

Related U.S. Application Data

(63) Continuation of application No. 18/183,773, filed on Mar. 14, 2023, which is a continuation of application No. 17/531,271, filed on Nov. 19, 2021, now Pat. No. 11,678,821, which is a continuation of application No. 17/113,560, filed on Dec. 7, 2020, which is a
(Continued)

(51) Int. Cl.
*A61B 5/145* (2006.01)
*A61B 5/00* (2006.01)
*G06Q 50/22* (2024.01)
*G16H 10/60* (2018.01)
(Continued)

(52) U.S. Cl.
CPC ...... *A61B 5/14532* (2013.01); *A61B 5/14546* (2013.01); *A61B 5/7282* (2013.01); *A61B 5/746* (2013.01); *G06Q 50/22* (2013.01); *G16H 10/60* (2018.01); *G16H 40/67* (2018.01); *G16H 80/00* (2018.01); *A61B 5/7275* (2013.01)

(58) Field of Classification Search
CPC ............ A61B 5/14532; A61B 5/14546; A61B 5/7282; A61B 5/746; A61B 5/7275; G06Q 50/22; G16H 10/60; G16H 40/67; G16H 80/00

See application file for complete search history.

(56) References Cited

U.S. PATENT DOCUMENTS 3,581,062 A    5/1971  Aston
3,926,760 A    12/1975 Allen et al.
(Continued)

FOREIGN PATENT DOCUMENTS

AU    2020284312       12/2021
CA    2 690 742 A1     12/2008
(Continued)

OTHER PUBLICATIONS

Breen, C. The iPhone Pocket Guide, 6th Edition, 2012, 96 pages.
(Continued)

*Primary Examiner* — Navin Natnithithadha
(74) *Attorney, Agent, or Firm* — WORKMAN NYDEGGER

(57) ABSTRACT

Methods and Devices to monitor the level of at least one analyte are provided.

30 Claims, 5 Drawing Sheets

Related U.S. Application Data continuation of application No. 15/916,255, filed on Mar. 8, 2018, now Pat. No. 10,856,785, which is a continuation of application No. 14/629,447, filed on Feb. 23, 2015, now Pat. No. 9,913,600, which is a continuation of application No. 13/448,287, filed on Apr. 16, 2012, now abandoned, which is a continuation of application No. 12/147,464, filed on Jun. 26, 2008, now Pat. No. 8,160,900.

(60) Provisional application No. 60/947,026, filed on Jun. 29, 2007.

(51) Int. Cl.
  *G16H 40/67* (2018.01)
  *G16H 80/00* (2018.01)

(56) References Cited

U.S. PATENT DOCUMENTS

| | | |
|---|---|---|
| 3,949,388 A | 4/1976 | Fuller |
| 4,036,749 A | 7/1977 | Anderson |
| 4,055,175 A | 10/1977 | Clemens et al. |
| 4,082,086 A | 4/1978 | Page et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,561,443 A | 12/1985 | Hogrefe et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,082,550 A | 1/1992 | Rishpon et al. |
| 5,106,365 A | 4/1992 | Hernandez |
| 5,108,889 A | 4/1992 | Smith |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,482,473 A | 1/1996 | Lord et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,555,190 A | 9/1996 | Derby et al. |
| 5,564,434 A | 10/1996 | Halperin et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,690,119 A | 11/1997 | Rytky et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,794,219 A | 8/1998 | Brown |
| 5,804,047 A | 9/1998 | Karube et al. |
| 5,807,375 A | 9/1998 | Gross et al. |
| 5,820,551 A | 10/1998 | Hill et al. |
| 5,822,715 A | 10/1998 | Worthington et al. |
| 5,875,186 A | 2/1999 | Belanger et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,919,141 A | 7/1999 | Money et al. |

(56) References Cited

U.S. PATENT DOCUMENTS

| | | |
|---|---|---|
| 5,925,021 A | 7/1999 | Castellano et al. |
| 5,942,979 A | 8/1999 | Luppino |
| 5,951,485 A | 9/1999 | Cyrus et al. |
| 5,951,521 A | 9/1999 | Mastrototaro et al. |
| 5,957,854 A | 9/1999 | Besson et al. |
| 5,959,529 A | 9/1999 | Kail, IV |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,987,353 A | 11/1999 | Khatchatrian et al. |
| 5,995,860 A | 11/1999 | Sun et al. |
| 6,001,067 A | 12/1999 | Shults et al. |
| 6,002,344 A | 12/1999 | Bandy et al. |
| 6,004,278 A | 12/1999 | Botich et al. |
| 6,022,315 A | 2/2000 | Iliff |
| 6,024,699 A | 2/2000 | Surwit et al. |
| 6,028,413 A | 2/2000 | Brockmann |
| 6,031,454 A | 2/2000 | Lovejoy et al. |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,268 A | 8/2000 | Inbar |
| 6,096,364 A | 8/2000 | Bok et al. |
| 6,103,033 A | 8/2000 | Say et al. |
| 6,115,622 A | 9/2000 | Minoz |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,130,623 A | 10/2000 | MacLellan et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,167,362 A | 12/2000 | Brown |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,248,065 B1 | 6/2001 | Brown |
| 6,248,067 B1 | 6/2001 | Causey, III et al. |
| 6,254,586 B1 | 7/2001 | Mann et al. |
| 6,266,551 B1 | 7/2001 | Osadchy et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,368,273 B1 | 4/2002 | Brown |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,437,692 B1 | 8/2002 | Petite et al. |
| 6,440,068 B1 | 8/2002 | Brown et al. |
| 6,442,432 B2 | 8/2002 | Lee |
| 6,461,496 B1 | 10/2002 | Feldman et al. |
| 6,471,689 B1 | 10/2002 | Joseph et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,595,929 B2 | 7/2003 | Stivoric et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,638,772 B1 | 10/2003 | Douglas et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |

(56) References Cited

U.S. PATENT DOCUMENTS

| | | |
|---|---|---|
| 6,658,396 B1 | 12/2003 | Tang et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,720,887 B1 | 4/2004 | Zunti |
| 6,721,582 B2 | 4/2004 | Trepagnier et al. |
| 6,730,025 B1 | 5/2004 | Platt |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,850,790 B2 | 2/2005 | Berner et al. |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,987,965 B2 | 1/2006 | Ng et al. |
| 6,989,750 B2 | 1/2006 | Shanks et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,774 B2 | 4/2006 | Freeman et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,046,153 B2 | 5/2006 | Oja et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,148,803 B2 | 12/2006 | Bandy et al. |
| 7,153,265 B2 | 12/2006 | Vachon |
| 7,155,290 B2 | 12/2006 | Von Arx et al. |
| 7,155,729 B1 | 12/2006 | Andrew et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,223,236 B2 | 5/2007 | Brown |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,242,294 B2 | 7/2007 | Warrior et al. |
| 7,258,666 B2 | 8/2007 | Brown |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,301,463 B1 | 11/2007 | Paterno |
| 7,310,544 B2 | 12/2007 | Brister et al. |
| 7,315,739 B2 | 1/2008 | Burch et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,329,239 B2 | 2/2008 | Safabash et al. |
| 7,335,294 B2 | 2/2008 | Heller et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,384,397 B2 | 6/2008 | Zhang et al. |
| 7,387,010 B2 | 6/2008 | Sunshine et al. |
| 7,392,167 B2 | 6/2008 | Brown |
| 7,399,277 B2 | 7/2008 | Saidara et al. |
| 7,402,153 B2 | 7/2008 | Steil et al. |
| 7,404,796 B2 | 7/2008 | Ginsberg |
| 7,406,105 B2 | 7/2008 | DelMain et al. |
| 7,419,573 B2 | 9/2008 | Gundel |

(56) References Cited

U.S. PATENT DOCUMENTS

| | | |
|---|---|---|
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,501,053 B2 | 3/2009 | Karinka et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,565,197 B2 | 7/2009 | Haubrich et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,624,028 B1 | 11/2009 | Brown |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,643,971 B2 | 1/2010 | Brown |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,684,999 B2 | 3/2010 | Brown |
| 7,689,440 B2 | 3/2010 | Brown |
| 7,693,485 B2 | 4/2010 | Parys |
| 7,697,967 B2 | 4/2010 | Stafford |
| 7,699,775 B2 | 4/2010 | Desai et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 | 6/2010 | Taub |
| 7,736,344 B2 | 6/2010 | Moberg et al. |
| 7,741,734 B2 | 6/2010 | Joannopoulos et al. |
| 7,751,864 B2 | 7/2010 | Buck, Jr. |
| 7,754,093 B2 | 7/2010 | Forrow et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,768,408 B2 | 8/2010 | Reggiardo et al. |
| 7,771,352 B2 | 8/2010 | Shults et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,797,367 B1 | 9/2010 | Gelvin et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,873,595 B2 | 1/2011 | Singh et al. |
| 7,877,274 B2 | 1/2011 | Brown |
| 7,877,276 B2 | 1/2011 | Brown |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,899,545 B2 | 3/2011 | John |
| 7,912,674 B2 | 3/2011 | Killoren Clark et al. |
| 7,914,460 B2 | 3/2011 | Melker et al. |
| 7,916,013 B2 | 3/2011 | Stevenson |
| 7,921,186 B2 | 4/2011 | Brown |
| 7,937,255 B2 | 5/2011 | Brown |
| 7,938,797 B2 | 5/2011 | Estes |
| 7,941,200 B2 | 5/2011 | Weinert et al. |
| 7,941,308 B2 | 5/2011 | Brown |
| 7,941,323 B2 | 5/2011 | Brown |
| 7,941,326 B2 | 5/2011 | Brown |
| 7,941,327 B2 | 5/2011 | Brown |
| 7,946,984 B2 | 5/2011 | Brister et al. |
| 7,946,985 B2 | 5/2011 | Mastrototaro et al. |
| 7,949,507 B2 | 5/2011 | Brown |
| 7,955,258 B2 | 6/2011 | Goscha et al. |
| 7,966,230 B2 | 6/2011 | Brown |
| 7,970,448 B2 | 6/2011 | Shults et al. |
| 7,970,620 B2 | 6/2011 | Brown |
| 7,972,267 B2 | 7/2011 | Brown |
| 7,972,296 B2 | 7/2011 | Braig et al. |
| 7,976,466 B2 | 7/2011 | Ward et al. |
| 7,978,063 B2 | 7/2011 | Baldus et al. |
| 7,979,259 B2 | 7/2011 | Brown |
| 7,979,284 B2 | 7/2011 | Brown |
| 7,996,158 B2 | 8/2011 | Hayter et al. |
| 7,999,674 B2 | 8/2011 | Kamen |
| 8,005,524 B2 | 8/2011 | Brauker et al. |
| 8,010,174 B2 | 8/2011 | Goode et al. |
| 8,010,256 B2 | 8/2011 | Oowada |
| 8,015,025 B2 | 9/2011 | Brown |
| 8,015,030 B2 | 9/2011 | Brown |
| 8,015,033 B2 | 9/2011 | Brown |
| 8,019,618 B2 | 9/2011 | Brown |
| 8,024,201 B2 | 9/2011 | Brown |
| 8,032,399 B2 | 10/2011 | Brown |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |

(56) References Cited

U.S. PATENT DOCUMENTS

| | | |
|---|---|---|
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,401,194 B2 | 3/2013 | Nierzwick et al. |
| 8,409,093 B2 | 4/2013 | Bugler |
| 8,444,560 B2 | 5/2013 | Hayter et al. |
| 8,457,703 B2 | 6/2013 | Al-Ali |
| 8,461,985 B2 | 6/2013 | Fennell et al. |
| 8,484,005 B2 | 7/2013 | Hayter et al. |
| 8,532,935 B2 | 9/2013 | Budiman |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,188 B2 | 12/2013 | Bernstein et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 8,924,159 B2 | 12/2014 | Taub et al. |
| 9,000,914 B2 | 4/2015 | Baker et al. |
| 9,060,719 B2 | 6/2015 | Hayter et al. |
| 9,211,065 B2 | 12/2015 | Marsh et al. |
| 9,289,179 B2 | 3/2016 | Hayter et al. |
| 9,344,777 B2 | 5/2016 | He et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 | 8/2017 | Hayter et al. |
| 9,801,541 B2 | 10/2017 | Mensinger et al. |
| 9,913,600 B2 | 3/2018 | Taub et al. |
| 9,980,140 B1 | 5/2018 | Spencer et al. |
| 10,375,222 B2 | 8/2019 | Mandapaka et al. |
| 10,855,788 B2 | 12/2020 | Arabo et al. |
| 10,856,785 B2 | 12/2020 | Taub et al. |
| 11,213,204 B2 | 1/2022 | Mensinger et al. |
| 11,264,133 B2 | 3/2022 | Bernstein et al. |
| 11,563,812 B2 | 1/2023 | Sloan et al. |
| 11,678,821 B2 | 6/2023 | Taub et al. |
| 11,991,175 B2 | 5/2024 | Rolfe et al. |
| 2001/0011224 A1 | 8/2001 | Brown |
| 2001/0020124 A1 | 9/2001 | Tamada |
| 2001/0037060 A1 | 11/2001 | Thompson et al. |
| 2001/0037366 A1 | 11/2001 | Webb et al. |
| 2001/0047604 A1 | 12/2001 | Valiulis |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0065454 A1 | 5/2002 | Lebel et al. |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0109621 A1 | 8/2002 | Khair et al. |
| 2002/0111832 A1 | 8/2002 | Judge |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0133107 A1 | 9/2002 | Darcey |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2002/0165443 A1 | 11/2002 | Mori |
| 2002/0173703 A1 | 11/2002 | Lebel et al. |
| 2002/0178126 A1 | 11/2002 | Beck et al. |
| 2002/0188748 A1 | 12/2002 | Blackwell et al. |
| 2003/0005464 A1 | 1/2003 | Gropper et al. |
| 2003/0021729 A1 | 1/2003 | Moller et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050009 A1 | 3/2003 | Kurisko et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0065536 A1 | 4/2003 | Hansen et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0134347 A1 | 7/2003 | Heller et al. |
| 2003/0144581 A1 | 7/2003 | Conn et al. |
| 2003/0147515 A1 | 8/2003 | Kai et al. |
| 2003/0153900 A1 | 8/2003 | Aceti et al. |
| 2003/0163351 A1 | 8/2003 | Brown |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2003/0217966 A1 | 11/2003 | Tapsak et al. |
| 2003/0229723 A1 | 12/2003 | Kangas et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015102 A1 | 1/2004 | Cummings et al. |
| 2004/0024553 A1 | 2/2004 | Monfre et al. |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0068230 A1 | 4/2004 | Estes et al. |
| 2004/0073266 A1 | 4/2004 | Haefner et al. |
| 2004/0078215 A1 | 4/2004 | Dahlin et al. |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0106860 A1 | 6/2004 | Say et al. |
| 2004/0111017 A1 | 6/2004 | Say et al. |
| 2004/0117204 A1 | 6/2004 | Mazar et al. |
| 2004/0117210 A1 | 6/2004 | Brown |
| 2004/0122353 A1 | 6/2004 | Shahmirian et al. |
| 2004/0127958 A1 | 7/2004 | Mazar et al. |
| 2004/0128225 A1 | 7/2004 | Thompson et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0147872 A1 | 7/2004 | Thompson |

(56) References Cited

U.S. PATENT DOCUMENTS

| | | |
|---|---|---|
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193090 A1 | 9/2004 | Lebel et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027181 A1 | 2/2005 | Goode et al. |
| 2005/0027182 A1 | 2/2005 | Siddiqui et al. |
| 2005/0027463 A1 | 2/2005 | Goode, Jr. et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0049501 A1 | 3/2005 | Conero et al. |
| 2005/0060194 A1 | 3/2005 | Brown |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0101912 A1 | 5/2005 | Faust et al. |
| 2005/0112169 A1 | 5/2005 | Brauker et al. |
| 2005/0113648 A1 | 5/2005 | Yang et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0148890 A1 | 7/2005 | Hastings |
| 2005/0154271 A1 | 7/2005 | Rasdal et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0228883 A1 | 10/2005 | Brown |
| 2005/0239154 A1 | 10/2005 | Feldman et al. |
| 2005/0239156 A1 | 10/2005 | Drucker et al. |
| 2005/0240245 A1 | 10/2005 | Bange et al. |
| 2005/0241957 A1 | 11/2005 | Mao et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0261563 A1 | 11/2005 | Zhou et al. |
| 2005/0277164 A1 | 12/2005 | Drucker et al. |
| 2005/0277912 A1 | 12/2005 | John |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0010014 A1 | 1/2006 | Brown |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0081469 A1 | 4/2006 | Lee |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0219576 A1 | 10/2006 | Jina |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0234202 A1 | 10/2006 | Brown |
| 2006/0235722 A1 | 10/2006 | Brown |
| 2006/0241975 A1 | 10/2006 | Brown |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0285660 A1 | 12/2006 | Brown |
| 2006/0285736 A1 | 12/2006 | Brown |
| 2006/0287691 A1 | 12/2006 | Drew |
| 2006/0287889 A1 | 12/2006 | Brown |
| 2006/0287931 A1 | 12/2006 | Brown |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0011320 A1 | 1/2007 | Brown |
| 2007/0016381 A1 | 1/2007 | Kamath et al. |
| 2007/0016445 A1 | 1/2007 | Brown |
| 2007/0017983 A1 | 1/2007 | Frank et al. |
| 2007/0021984 A1 | 1/2007 | Brown |

(56) References Cited

U.S. PATENT DOCUMENTS

| | | |
|---|---|---|
| 2007/0027381 A1 | 2/2007 | Stafford |
| 2007/0027383 A1 | 2/2007 | Peyser et al. |
| 2007/0027507 A1 | 2/2007 | Burdett et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0043279 A1 | 2/2007 | Mannheimer et al. |
| 2007/0055799 A1 | 3/2007 | Koehler et al. |
| 2007/0056858 A1 | 3/2007 | Chen et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0060870 A1 | 3/2007 | Tolle et al. |
| 2007/0060979 A1 | 3/2007 | Strother et al. |
| 2007/0061167 A1 | 3/2007 | Brown |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0109117 A1 | 5/2007 | Heitzmann et al. |
| 2007/0118030 A1 | 5/2007 | Bruce et al. |
| 2007/0118588 A1 | 5/2007 | Brown |
| 2007/0129621 A1 | 6/2007 | Kellogg et al. |
| 2007/0142727 A1 | 6/2007 | Zhang et al. |
| 2007/0149875 A1 | 6/2007 | Ouyang et al. |
| 2007/0156033 A1 | 7/2007 | Causey, III et al. |
| 2007/0156457 A1 | 7/2007 | Brown |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0176867 A1 | 8/2007 | Reggiardo et al. |
| 2007/0179434 A1 | 8/2007 | Weinert et al. |
| 2007/0191701 A1 | 8/2007 | Feldman et al. |
| 2007/0191702 A1 | 8/2007 | Yodfat et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0207750 A1 | 9/2007 | Brown et al. |
| 2007/0208244 A1 | 9/2007 | Brauker et al. |
| 2007/0208246 A1 | 9/2007 | Brauker et al. |
| 2007/0213605 A1 | 9/2007 | Brown |
| 2007/0213657 A1 | 9/2007 | Jennewine et al. |
| 2007/0219480 A1 | 9/2007 | Kamen et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0251835 A1 | 11/2007 | Mehta et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0288265 A1 | 12/2007 | Quinian et al. |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0004904 A1 | 1/2008 | Tran |
| 2008/0009692 A1 | 1/2008 | Stafford |
| 2008/0009805 A1 | 1/2008 | Ethelfeld |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058773 A1 | 3/2008 | John |
| 2008/0060955 A1 | 3/2008 | Goodnow |
| 2008/0061961 A1 | 3/2008 | John |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097246 A1 | 4/2008 | Stafford |
| 2008/0102441 A1 | 5/2008 | Chen et al. |
| 2008/0103447 A1 | 5/2008 | Reggiardo et al. |
| 2008/0108942 A1 | 5/2008 | Brister et al. |
| 2008/0114228 A1 | 5/2008 | McCluskey et al. |
| 2008/0114229 A1 | 5/2008 | Brown |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0139910 A1 | 6/2008 | Mastrototaro et al. |
| 2008/0148873 A1 | 6/2008 | Wang |
| 2008/0154099 A1 | 6/2008 | Aspel et al. |
| 2008/0161666 A1 | 7/2008 | Feldman et al. |
| 2008/0167572 A1 | 7/2008 | Stivoric et al. |
| 2008/0169904 A1 | 7/2008 | Schulman et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0218180 A1 | 9/2008 | Waffenschmidt et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255438 A1 | 10/2008 | Saidara et al. |

(56) References Cited

U.S. PATENT DOCUMENTS

| | | |
|---|---|---|
| 2008/0262469 A1 | 10/2008 | Brister et al. |
| 2008/0267823 A1 | 10/2008 | Wang et al. |
| 2008/0269571 A1 | 10/2008 | Brown |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278332 A1 | 11/2008 | Fennell et al. |
| 2008/0278333 A1 | 11/2008 | Fennell et al. |
| 2008/0281179 A1 | 11/2008 | Fennell et al. |
| 2008/0287761 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294024 A1 | 11/2008 | Cosentino et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312512 A1 | 12/2008 | Brukalo et al. |
| 2008/0312518 A1 | 12/2008 | Jina et al. |
| 2008/0314395 A1 | 12/2008 | Kovatchev et al. |
| 2008/0319085 A1 | 12/2008 | Wright et al. |
| 2008/0319294 A1 | 12/2008 | Taub et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0036747 A1 | 2/2009 | Hayter et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0062633 A1 | 3/2009 | Brauker et al. |
| 2009/0062635 A1 | 3/2009 | Brauker et al. |
| 2009/0063964 A1 | 3/2009 | Huang et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0093687 A1 | 4/2009 | Telfort et al. |
| 2009/0099427 A1 | 4/2009 | Jina et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0112478 A1 | 4/2009 | Mueller, Jr. et al. |
| 2009/0112626 A1 | 4/2009 | Talbot et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143661 A1 | 6/2009 | Taub et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0237216 A1 | 9/2009 | Twitchell, Jr. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0248380 A1 | 10/2009 | Brown |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0004522 A1 | 1/2010 | Varela |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |

(56) References Cited

U.S. PATENT DOCUMENTS

| | | |
|---|---|---|
| 2010/0045425 A1 | 2/2010 | Chivallier |
| 2010/0045465 A1 | 2/2010 | Brauker et al. |
| 2010/0049024 A1 | 2/2010 | Saint et al. |
| 2010/0052899 A1 | 3/2010 | Bruce |
| 2010/0057041 A1 | 3/2010 | Hayter et al. |
| 2010/0063373 A1 | 3/2010 | Kamath et al. |
| 2010/0064764 A1 | 3/2010 | Hayter et al. |
| 2010/0076283 A1 | 3/2010 | Simpson et al. |
| 2010/0076284 A1 | 3/2010 | Bernstein et al. |
| 2010/0081905 A1 | 4/2010 | Bommakanti et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094111 A1 | 4/2010 | Heller et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0111066 A1 | 5/2010 | Mehta |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141429 A1 | 6/2010 | Bruegger et al. |
| 2010/0141656 A1 | 6/2010 | Krieftewirth |
| 2010/0145172 A1 | 6/2010 | Petisce et al. |
| 2010/0146300 A1 | 6/2010 | Brown |
| 2010/0152554 A1 | 6/2010 | Steine et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179399 A1 | 7/2010 | Goode et al. |
| 2010/0179400 A1 | 7/2010 | Brauker et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179405 A1 | 7/2010 | Goode et al. |
| 2010/0179407 A1 | 7/2010 | Goode et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185073 A1 | 7/2010 | Goode et al. |
| 2010/0185074 A1 | 7/2010 | Goode et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0213057 A1 | 8/2010 | Feldman et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0257490 A1 | 10/2010 | Lyon et al. |
| 2010/0268157 A1 | 10/2010 | Wehba et al. |
| 2010/0274111 A1 | 10/2010 | Say et al. |
| 2010/0274218 A1 | 10/2010 | Yodfat et al. |
| 2010/0280441 A1 | 11/2010 | Willinska et al. |
| 2010/0280782 A1 | 11/2010 | Harper |
| 2010/0298686 A1 | 11/2010 | Reggiardo et al. |
| 2010/0302979 A1 | 12/2010 | Reunamäki |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2010/0327063 A1 | 12/2010 | Medina et al. |
| 2011/0003610 A1 | 1/2011 | Key et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0009813 A1 | 1/2011 | Rankers |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0031986 A1 | 2/2011 | Bhat et al. |
| 2011/0040163 A1 | 2/2011 | Telson et al. |
| 2011/0044333 A1 | 2/2011 | Sicurello et al. |
| 2011/0077490 A1 | 3/2011 | Simpson et al. |
| 2011/0082484 A1 | 4/2011 | Saravia et al. |
| 2011/0105955 A1 | 5/2011 | Yudovsky et al. |
| 2011/0106126 A1 | 5/2011 | Love et al. |
| 2011/0112696 A1 | 5/2011 | Yodfat et al. |
| 2011/0125000 A1 | 5/2011 | Rantala |
| 2011/0148905 A1 | 6/2011 | Simmons et al. |
| 2011/0152637 A1 | 6/2011 | Kateraas et al. |
| 2011/0173308 A1 | 7/2011 | Gutekunst |
| 2011/0177780 A1 | 7/2011 | Sato et al. |
| 2011/0178717 A1 | 7/2011 | Goodnow et al. |
| 2011/0190603 A1 | 8/2011 | Stafford |
| 2011/0191044 A1 | 8/2011 | Stafford |
| 2011/0193704 A1 | 8/2011 | Harper et al. |
| 2011/0202495 A1 | 8/2011 | Gawlick |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0282327 A1 | 11/2011 | Kellogg et al. |
| 2011/0282671 A1 | 11/2011 | Dicks et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0320130 A1 | 12/2011 | Valdes et al. |
| 2012/0003933 A1 | 1/2012 | Baker et al. |
| 2012/0035448 A1 | 2/2012 | Taub et al. |
| 2012/0078071 A1 | 3/2012 | Bohm et al. |
| 2012/0108931 A1 | 5/2012 | Taub et al. |
| 2012/0108934 A1 | 5/2012 | Valdes et al. |
| 2012/0123227 A1 | 5/2012 | Sun et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179017 A1 | 7/2012 | Satou et al. |
| 2012/0182917 A1 | 7/2012 | Edlund |
| 2012/0200410 A1 | 8/2012 | Taub et al. |
| 2012/0209099 A1 | 8/2012 | Ljuhs et al. |
| 2012/0215462 A1 | 8/2012 | Goode et al. |
| 2012/0237022 A1 | 9/2012 | Berson et al. |
| 2012/0255875 A1 | 10/2012 | Vicente et al. |

(56) References Cited

U.S. PATENT DOCUMENTS

| | | |
|---|---|---|
| 2012/0260323 A1 | 10/2012 | San Vicente et al. |
| 2012/0265035 A1 | 10/2012 | Bohm et al. |
| 2012/0313785 A1 | 12/2012 | Hanson et al. |
| 2013/0035575 A1 | 2/2013 | Mayou et al. |
| 2013/0078912 A1 | 3/2013 | San Vicente et al. |
| 2013/0113632 A1 | 5/2013 | Bernstein et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0310896 A1 | 11/2013 | Mass |
| 2014/0088382 A1 | 3/2014 | Bernstein et al. |
| 2014/0221966 A1 | 8/2014 | Buckingham et al. |
| 2014/0266776 A1 | 9/2014 | Miller et al. |
| 2014/0266785 A1 | 9/2014 | Miller et al. |
| 2014/0273821 A1 | 9/2014 | Miller et al. |
| 2014/0273858 A1 | 9/2014 | Panther et al. |
| 2014/0275898 A1 | 9/2014 | Taub et al. |
| 2014/0313052 A1 | 10/2014 | Yarger et al. |
| 2014/0379273 A1 | 12/2014 | Petisce et al. |
| 2015/0038818 A1 | 2/2015 | Cole |
| 2015/0089222 A1 | 3/2015 | White et al. |
| 2015/0118658 A1 | 4/2015 | Mayou et al. |
| 2015/0123810 A1 | 5/2015 | Hernandez-Rosas et al. |
| 2015/0164391 A1 | 6/2015 | Hernandez-Rosas et al. |
| 2015/0164392 A1 | 6/2015 | Taub et al. |
| 2015/0205947 A1 | 7/2015 | Berman et al. |
| 2015/0207796 A1 | 7/2015 | Love et al. |
| 2015/0241407 A1 | 8/2015 | Ou et al. |
| 2015/0289124 A1 | 10/2015 | Palin et al. |
| 2016/0066826 A1 | 3/2016 | Larvenz et al. |
| 2016/0081597 A1 | 3/2016 | Bhavaraju et al. |
| 2016/0165649 A1 | 6/2016 | Polo et al. |
| 2016/0210099 A1 | 7/2016 | Hampapuram et al. |
| 2016/0234020 A1 | 8/2016 | Nix |
| 2018/0192927 A1 | 7/2018 | Taub et al. |
| 2018/0325434 A1 | 11/2018 | Bernstein et al. |
| 2021/0000396 A1 | 1/2021 | Bernstein et al. |
| 2021/0151182 A1 | 5/2021 | Bernstein et al. |
| 2021/0169384 A1 | 6/2021 | Taub et al. |
| 2022/0068473 A1 | 3/2022 | Miller et al. |
| 2022/0071526 A1 | 3/2022 | Taub et al. |
| 2022/0095968 A1 | 3/2022 | Wang et al. |
| 2023/0210413 A1 | 7/2023 | Taub et al. |
| 2024/0298933 A1 | 9/2024 | Taub et al. |
| 2024/0423515 A1 | 12/2024 | Taub et al. |

FOREIGN PATENT DOCUMENTS

| | | |
|---|---|---|
| DE | 4401400 | 7/1995 |
| DE | 202015010002 U1 | 12/2022 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2407094 | 1/2012 |
| EP | 3158922 | 4/2017 |
| EP | 3240352 A1 | 11/2017 |
| EP | 3 435 866 | 11/2020 |
| EP | 3 831 282 B1 | 6/2021 |
| EP | 2 939 158 | 3/2022 |
| EP | 3 730 045 | 3/2022 |
| EP | 3831282 | 3/2022 |
| EP | 3 977 921 | 4/2022 |
| EP | 3 797 685 | 5/2022 |
| JP | 4469504 | 5/2010 |
| WO | WO 1996/025089 | 8/1996 |
| WO | WO 1996/035370 | 11/1996 |
| WO | WO 1998/035053 | 8/1998 |
| WO | WO 99/58190 | 11/1999 |
| WO | WO 1999/056613 | 11/1999 |
| WO | WO 2000/049940 | 8/2000 |
| WO | WO 2000/059370 | 10/2000 |
| WO | WO 2000/074753 | 12/2000 |
| WO | WO 2000/078992 | 12/2000 |
| WO | WO 2001/052935 | 7/2001 |
| WO | WO 2001/054753 | 8/2001 |
| WO | WO 02/15778 | 2/2002 |
| WO | WO 2002/016905 | 2/2002 |
| WO | WO 2002/058537 | 8/2002 |
| WO | WO 02/071305 | 9/2002 |
| WO | WO 03/026728 | 4/2003 |
| WO | WO 2003/082091 | 10/2003 |
| WO | WO 2004/006982 | 1/2004 |
| WO | WO 2005/018450 | 3/2005 |
| WO | WO 2005/046780 | 5/2005 |
| WO | WO 2006/024671 | 3/2006 |
| WO | WO 2006/040083 | 4/2006 |
| WO | WO 2006/094513 | 9/2006 |
| WO | WO 2006/121921 | 11/2006 |
| WO | WO 2007/002189 | 1/2007 |
| WO | WO 2007/097754 | 8/2007 |
| WO | WO 2007/104755 A1 | 9/2007 |
| WO | WO 2008/001366 | 1/2008 |
| WO | WO 2008/065646 | 6/2008 |
| WO | WO 2008/073813 | 6/2008 |
| WO | WO 2008/086541 | 7/2008 |
| WO | WO 2008/114223 | 9/2008 |
| WO | WO 2008/115409 | 9/2008 |
| WO | WO 2008/144325 A1 | 11/2008 |
| WO | WO 2008/157821 | 12/2008 |
| WO | WO 2009/007287 | 1/2009 |
| WO | WO 2009/035773 | 3/2009 |
| WO | WO 2009/039013 | 3/2009 |
| WO | WO 2009/051832 | 4/2009 |
| WO | WO 2009/105709 | 8/2009 |
| WO | WO 2010/077329 | 7/2010 |
| WO | WO 2012/154286 A1 | 11/2012 |
| WO | WO 2013/044153 | 3/2013 |
| WO | WO 2013/069894 A1 | 5/2013 |
| WO | WO 2013/090731 | 6/2013 |
| WO | WO 2013/090791 A1 | 6/2013 |
| WO | WO 2014/011488 | 1/2014 |
| WO | WO 2014/105631 A2 | 7/2014 |
| WO | WO 2014/158405 A2 | 10/2014 |
| WO | WO 2014/165172 A1 | 10/2014 |
| WO | WO 2014/179343 | 11/2014 |
| WO | WO 2015/046823 | 4/2015 |
| WO | WO 2015/069797 | 5/2015 |
| WO | WO 2015/194381 | 12/2015 |
| WO | WO 2016/064184 A1 | 4/2016 |
| WO | WO 2016/092448 A1 | 6/2016 |
| WO | WO 2016/101774 A1 | 6/2016 |
| WO | WO 2017/172781 | 10/2017 |
| WO | WO 2018/017484 A1 | 1/2018 |
| WO | WO 2018/075333 | 4/2018 |
| WO | WO 2020/242964 | 12/2020 |

OTHER PUBLICATIONS

Declaration of Dr. Sayfe Kiael, Ph.D., Inter Partes Review of U.S. Pat. No. 10,375,222, 100 pages (2024).
Declaration of Lane Desborough, 2024, 150 pages.
DeSalvo, D. et al., "Remote Glucose Monitoring in Camp Setting Reduces the Risk of Prolonged Nocturnal Hypoglycemia" Diabetes Technology & Therapeutics, vol. 16, No. 1, 2014, p. 1-10.
File History of U.S. Pat. No. 11,213,204, Issued Jan. 4, 2022.
File History of U.S. Pat. No. 9,801,541, Issued Oct. 31, 2017.
Keith-Hynes, P., et al., "The Diabetes Assistant: A Smartphone-Based System for Real-Time Control of Blood Glucose" Electronics, 2014, pp. 609-623.
McDaniels, D., et al., "Remote Management of Cardiac Patients: The Forefront of a New Standard" Modern Healthcare, 2011, 6 pages.
MySentry™ User Guide, Medtronic Minimed, 2010, 80 pages.
Paradigm® Real-Time Revel™ Insulin Pump User Guide, Medtronic Minimed, 2009, 179 pages.
Place, J., et al., "DiAs Web Monitoring: A. Real-Time Remote Monitoring System Designed for Artificial Pancreas Outpatient

(56) References Cited

OTHER PUBLICATIONS

Trials" Journal of Diabetes Science and Technology, vol. 7, No. 6, 2013, pp. 1427-1435.
Press Release, Medtronic, "Medtronic Launches First-of-Its Kind mySentry™ Remote Glucose Monitor" 2012, 8 pages.
Wettlaufer, G., "Merlin.Net Automation of External Reports Verification Process" 2010, 53 pages.
U.S. Appl. No. 60/587,787, filed Jul. 13, 2004, Brister, et al.
U.S. Appl. No. 60/614,683, filed Sep. 30, 2004, Brister, et al.
U.S. Appl. No. 14/629,447 (U.S. Pat. No. 9,913,600), filed Feb. 23, 2015 (Mar. 13, 2018).
U.S. Appl. No. 15/916,255 (U.S. Pat. No. 10,856,785), filed Mar. 8, 2018 (Dec. 8, 2020).
U.S. Appl. No. 17/113,560 (2021/0169384), filed Dec. 7, 2020 (Jun. 10, 2021).
U.S. Appl. No. 17/531,271 (U.S. Pat. No. 11,678,821), filed Nov. 19, 2021 (Jun. 20, 2023).
U.S. Appl. No. 18/183,773 (US 2023/0210413), filed Mar. 14, 2023 (Jul. 6, 2023).
U.S. Appl. No. 18/183,773, May 30, 2024 Request for Continued Examination (RCE).
U.S. Appl. No. 18/183,773, Apr. 15, 2024 Notice of Allowance.
U.S. Appl. No. 18/183,773, Mar. 20, 2024 Notice of Allowance.
U.S. Appl. No. 18/183,773, Feb. 6, 2024 Response to Non-Final Office Action.
U.S. Appl. No. 18/183,773, Sep. 8, 2023 Non-Final Office Action.
U.S. Appl. No. 17/531,271, May 4, 2023 Issue Fee Payment.
U.S. Appl. No. 17/531,271, May 2, 2023 Notice of Allowance.
U.S. Appl. No. 17/531,271, Apr. 18, 2023 Request for Continued Examination (RCE).
U.S. Appl. No. 17/531,271, Feb. 23, 2023 Notice of Allowance.
U.S. Appl. No. 17/531,271, Feb. 9, 2023 Request for Continued Examination (RCE).
U.S. Appl. No. 17/531,271, Dec. 21, 2022 Notice of Allowance.
U.S. Appl. No. 17/531,271, Nov. 23, 2022 Request for Continued Examination (RCE).
U.S. Appl. No. 17/531,271, Oct. 13, 2022 Notice of Allowance.
U.S. Appl. No. 17/531,271, Sep. 19, 2022 Request for Continued Examination (RCE).
U.S. Appl. No. 17/531,271, Jul. 25, 2022 Notice of Allowance.
U.S. Appl. No. 17/531,271, Jun. 28, 2022 Response to Non-Final Office Action.
U.S. Appl. No. 17/531,271, Mar. 28, 2022 Non-Final Office Action.
U.S. Appl. No. 15/916,255, Nov. 5, 2020 Issue Fee Payment.
U.S. Appl. No. 15/916,255, Aug. 5, 2020 Notice of Allowance.
U.S. Appl. No. 15/916,255, Jul. 23, 2020 Response to Non-Final Office Action.
U.S. Appl. No. 15/916,255, Apr. 23, 2020 Non-Final Office Action.
U.S. Appl. No. 14/629,447, Jan. 16, 2018 Issue Fee Payment.
U.S. Appl. No. 14/629,447, Dec. 5, 2017 Notice of Allowance.
U.S. Appl. No. 14/629,447, Nov. 6, 2017 Response to Non-Final Office Action.
U.S. Appl. No. 14/629,447, Aug. 10, 2017 Non-Final Office Action.
"Encryption and Authentication Overview", Bluetooth Specification, Version 4.0, vol. 6, 1 page (2010).
"RFID Handbook: Fundamentals and Applications in Contactless Smart Cards and Identification", Second Edition, Klaus Finkenzeller, 114 pages (2003).
"Setting Your Sensor Settings" retrieved from "https://web.archive.org/web/20160803065621/http://www.medtronicdiabetes.com:80/customer-support/device-settings-and-features/sensor-settings/setting-sensor-settings" on Nov. 18, 2022, 5 pages.
"Specification of the Bluetooth System, Experience More", Bluetooth Specification, Version 4.0, vol. 0, 89 pages (2010).
"Within Definition & Meaning" retrieved from "https://www.dictionary.com/browse/within" on Sep. 9, 2022, 5 pages.
Armour, J. C., et al., "Application of Chronic Intravascular Blood Glucose Sensor in Dogs", Diabetes, vol. 39, 1990, pp. 1519-1526.
Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.
Bennion, N., et al., "Alternate Site Glucose Testing: A Crossover Design", Diabetes Technology & Therapeutics, vol. 4, No. 1, 2002, pp. 25-33.
Blank, T. B., et al., "Clinical Results from a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Bluetooth Specification, Version 4.0, 2,303 pages (2010).
Brooks, S. L., et al., "Development of an On-Line Glucose Sensor for Fermentation Monitoring", Biosensors, vol. 3, 1987/88, pp. 45-56.
Cass, A. E., et al., "Ferrocene-Medicated Enzyme Electrode for Amperometric Determination of Glucose", Analytical Chemistry, vol. 56, No. 4, 1984, 667-671.
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Chuang et al., "Pilot Studies of Transdermal Continuous Glucose Measurement in Outpa-tient Diabetic Patients and in Patients during and after Cardiac Surgery," Journal of Diabetes Science and Technology, 595-602 (2008).
Compare Specification—Apple iPhone 6 vs. Apple iPhone 6 Plus—https://www.gsmarena.com/compare.php3?idPhone1=6378&idPhone2=6665, 2 pages, Jan. 31, 2022.
Cornelius, Cory, "Usable Security for Wireless Body-Area Networks" (2013). Dartmouth College PhD Dissertations. 42.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Cunningham, David and Stenken, Julie, In Vivo Glucose Sensing, Chemical Analysis, vol. 174 (2010).
Dartmouth Library, Email Confirmation re availability of PhD thesis "Usable Security for Wireless Bod-Area Networks" by C. Cory.
Dexcom G4® Platinum, Continuous Glucose Monitoring System, User's Guide, Dexcom, Inc., 161 pages (2015).
Dexcom G5 Mobile Continuous Glucose Monitoring System, Advisory Committee Briefing Materials, Clinical Chemistry and Clinical Toxicology Devices Panel, 283 pages (2016).
Dexcom G5 User Guide, Dexcom, Inc., 265 pages (2015).
Dexcom G5™ Mobile, Continuous Glucose Monitoring System, User Guide, Dexcom, Inc., 264 pages (2015).
Dexcom News Releases—FDA Approves Dexcom G4 Platinum Continuous Glucose Monitoring System with Share—https://www.dexcom.com/en-us/news/fda-approves-dexcom-g4-platinum-continuous-glucose-monitoring-system-share, Dexcom, Inc., 2 pages, Jan. 26, 2015.
Dexcom Press Releasez—FDA Approves Dexcom G5® Mobile Continuous Glucose Moni-toring System—https://www.dexcom.com/news/1257506247-fda-approves-dexcom-g5®-mobile-continuous-glucose-monitoring-system, Dexcom, Inc., 4 pages, Aug. 24, 2015.
Dexcom, Inserting Sensor, Instructions for Use, Dexcom, Inc., 2 pages (2021).
DexcomG7, Operational Manual, User Guide, Dexcom, Inc., 179 pages (2022) (with an English Abstract).
DexcomG7, Receiver: Start Here, Operational Manual, Dexcom, Inc., 8 pages (2022).
DexcomG7, Start Here, Operational Manual, Dexcom, Inc. 9 pages (2022) (with an English Abstract).
Diallo, A.S., et al., "A Secure Authentication Scheme for Bluetooth Connection", 5$^{th}$ International Conference on Computer & Communication Engineering (2014).
Ellmerer, Martin, "Measurement of interstitial albumin in human skeletal muscle and adipose tissue by open-flow microperfusion", Am. J. Physiol Endocrinol. Metab. 278: E352-E356 (2000).
Encyclopedia Britannica, Science & Tech, Bluetooth Definition, 5 pages, (Oct. 14, 2023).
Evans, et al., "Clinical temperature acquisition using proximity telemetry", J. Biomed. Eng., 13:83-86 (1991).

(56) References Cited

OTHER PUBLICATIONS

Excerpts from the "German Health Report Diabetes 2023" of the German Diabetes Socie-ty, 14 pages (2022) (with an English Abstract).
Exhibit B-22.pdf—Opponent's Written Response in Opposition of EP 3 730 045, Sep. 27, 2023, 43 pages.
Farid Dowla, "The Basics of Radio Frequency Identification (RFID) Technology", Handbook of RF & Wireless Technologies, Chapter 14, 44 pages (2004).
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Ferro, et al., "Bluetooth and Wi-fi Wireless Protocols: A Survey and a Comparison", IEEE Wireless Communications, pp. 1-24 (2004).
Ferro, et al., "Bluetooth and Wi-fi Wireless Protocols: A Survey and a Comparison", IEEE Wireless Communications, 12(1):12-26 (2005).
U.S. Pat. No. 10,375,222, issued Aug. 6, 2019, 442 pages.
U.S. Appl. No. 60/587,787, filed Jul. 13, 2004, 69 pages.
Finkenzeller, "RFID Handbook: Fundamentals and Applications in Contactless Smart Cards, Radio Frequency Identification and Near-Field Communication", Third Edition, 4 pages (2010).
FreeStyle Libre Flash Glucose Monitoring System, User's Manual, Abbott Diabetes Care Ltd., 124 pages (2014).
Garg, S., et al., "Improvement in Glycemic Excursions with a Transcutaneous, Real-Time Continuous Glucose Sensor", Diabetes Care, vol. 29, No. 1, 2006, pp. 44-50.
German Infringement Complaint dated Jul. 15, 2021.
German Infringement Complaint Service addressed to Dexcom Deutschland GmbH.
Gomez, Carles, et al., Overview an Evaluation of Bluetooth Low Energy: An Emerging Low-Power Wireless Technology, Sensors (12) 2012.
Guder, W.G., et al., Samples: From the patient to the Laboratory, $3^{rd}$ revised edition 2003.
Hamblen, "A short history of NFC: Where Near Field Communication has come from.", 2 pages, Dec. 19, 2012.
Heller, et al., "Electrochemical Glucose Sensors and Their Applications in Diabetes Management", Chemical Reviews, 108(7):2482-2505 (2008).
Higson, S.P.J. and Vadgama, P.M., Biosensors: a viable monitoring technology? Med & Biol. Eng. & Comput., 1994, 32, 601-609.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jovanovic, L., "The Role of Continuous Glucose Monitoring in Gestational Diabetes Mellitus", Diabetes Technology & Therapeutics, vol. 2, Sup. 1, 2000, pp. S67-S71.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Klueh, et al., "Inflammation and Glucose Sensors: Use of Dexamethasone to Extend Glu-cose Sensor Function and Life Span in Vivo", Journal of Diabetes Science and Technolo-gy, 1(4):496-504 (2007).
Li, Y., et al., "In Vivo Release From a Drug Delivery MEMS Device", Journal of Controlled Release, vol. 100, 2004, 99. 211-219.
Liang, et al., "An implantable bi-directional wireless transmission system for transcutaneous biological signal recording", Physiological Measurement, 26:83-97 (2005).
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain the Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
McCartney et al., "In vivo glucose sensing for diabetes management: progress towards non-invasive monitoring," BMJ, vol. 319, 4 pages (1999).
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, vol. 3, No. 3, 2001, pp. 367-376.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Microchip, microID® 13.56 MHz RFID, System Design Guide, Microchip Technology Inc., 214 pages (2004).
Miniholde, Roland, Near Field Communication (NFC) Technology and Measurements White Paper, Rohde & Schwarz (Jun. 2011).
Mohanty and Kougianos, Biosensors: A tutorial review, IEEE Potentials, pp. 35-46 (2006).
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.
Near Field Communication (NFC) Technology and Measurements, White Paper, Rohde & Schwarz, 1 page (2011).
Near Field Communication (NFC) Technology and Measurements, White Paper, Rohde & Schwarz, 18 pages (2011).
NFC Forum Bluetooth Special Interest Group, Bluetooth® Secure Simple Pairing Using NFC, 39 pages (2014).
Omre, "Bluetooth Low Energy: Wireless Connectivity for Medical Monitoring," Journal of Diabetes Science and Technology, vol. 4, Issue 2, 457-463 (Mar. 2010).
Padgette et al., "Guide to Bluetooth Security—Recommendations of the National Institute of Standards and Technology," National Institute of Standards and Technology, U.S. Dept. Commerce, 800-121, Rev 1, 48 pages (May 2017).
Padgette, John, et al., Recommendations of the National Institute of Standards and Technology, Guide to Bluetooth Security Jun. 2012.
Panteleon, A. E., et al., "The Role of the Independent Variable to Glucose Sensor Calibration", Diabetes Technology & Therapeutics, vol. 5, No. 3, 2003, pp. 401-410.
Parker, R., et al., "Robust H∞ Glucose Control in Diabetes Using a Physiological Model", AIChE Journal, vol. 46, No. 12, 2000, pp. 2537-2549.
Pete Sorrells, "Passive RFID Basics", Microchip Technology Inc., DS00680B, pp. 1-5 (1998).
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.

(56) References Cited

OTHER PUBLICATIONS

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Press Coverage of FreeStyle Libre launch, Antonia Giese, retrieved from https://www.bild.de/ratgeber/gesundheit/diabetes/hightech-zucker-sensor-diabetes-test-freestyle-libre-flash-37732134.bild.html, 8 pages Sep. 20, 2014 (with an English Abstract).
Quinn, C. P., et al., "Kinetics of Glucose Delivery to Subcutaneous Tissue in Rats Measured with 0.3-mm Amperometric Microsensors", The American Physiological Society, 1995, E155-E161.
Radio Frequency Identification RFID, AIM Inc. White Paper, Document Version 1.2, pp. 1-17 (2001).
Rivest, R.L., et al., A Method for Obtaining Digital Signatures and Public-Key Cryptosystems, Laboratory for Computer Science, Massachusetts Institute of Technology.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schaupp, L, Direct access to interstitial fluid in adipose tissue in humans by use of open-flow microperfusion, downloaded from journals.physiology.org/journal/ajpendo on Oct. 4, 2021.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Seymour, Burch, et al., Bluetooth Master/Slave Communications and Sniff/Sniff Sub-rating Modes White Paper, Aug. 14, 2008.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device with Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas with Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sola-Gazagnes, et al., "Emergent technologies applied to diabetes: What do we need to integrate continuous glucose monitoring into daily practice? *Where the long-term use of continuous glucose monitoring stands in 2011*", Diabetes & Metabolism, vol. 37, pp. S65-S70 (2011).
Specification of the Bluetooth System, Experience More, Master Table of Contents & Compliance Requirements, 134 pages (Jun. 2010).
Specification of the Bluetooth System, Experience More, Specification vol. 0, Covered Core Package Version: 4.0, 2 302 pages (2010).
Specification of the Bluetooth System, Experience More, Specification vol. 0, Covered Core Package Version: 4.0, 41 pages (2010).
Specification of the Bluetooth System, Version 4.0 [vol. 0] 2010.
Specification of the Bluetooth System, Version 4.1 [vol. 0] 2013.
Specification of the Bluetooth System, Version 4.2 [vol. 0] 2014.
Specification of the Bluetooth System, Wireless connections made easy, Master Table of Contents & Compliance Requirements, 92 pages (Nov. 2003).
Specification of the Samsung Galaxy Alpha, Samsung Newsroom Deutschland—http://www.samsung.de/galaxyalpha, 6 pages, Aug. 13, 2014 (with an English Abstract).
Stallings, William, Cryptography and Network Security Principles and Practice, Prentice Hall, $5^{th}$ Edition.
Sternberg, R., et al., "Study and Development of Multilayer Needle-Type Enzyme-Based Glucose Microsensors", Biosensors, vol. 4, 1988, pp. 27-40.
Strickland, Ray, et al., Bluetooth Continuous Glucose Monitory Profile, Bluetooth Special Interest Group, v1.0.1, Dec. 15, 2015.
Strommer et al., "Application of Near Field Communication for Health Monitoring in Daily Life," Proceedings of the 28th IEEE, EMBS Annual International Conference New York City, USA, Aug. 30-Sep. 3, 2006, 3246-3249.
The New Shorter Oxford English Dictionary, p. 50.
Thompson, M., et al., "In Vivo Probes: Problems and Perspectives", Clinical Biochemistry, vol. 19, 1986, pp. 255-261.
Townsend et al., "Getting Started with Bluetooth Low Energy—Tools and Techniques for Low-Power Networking," O'Reilly Media, Inc., 180 pages (2014).
Townsend, Kevin, et al., Getting Started with Bluetooth Low Energy, www.allitebooks.com.
Translation of German Infringement Complaint dated Sep. 9, 2021.
Turner, A., et al., "Diabetes Mellitus: Biosensors for Research and Management", Biosensors, vol. 1, 1985, pp. 85-115.
U.S. Appl. No. 12/147,464, Notice of Allowance mailed Jan. 24, 2012.
U.S. Appl. No. 12/147,464, Office Action mailed Oct. 23, 2014.
U.S. Appl. No. 14/629,447, Notice of Allowance mailed Dec. 5, 2017.
U.S. Appl. No. 14/629,447, Office Action mailed Aug. 10, 2017.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Wang et al. "A Feasible IMD Communication Protocol: Security without Obscurity," School of Engineering and Computing Sciences, NYIT Research Experience for Under-graduates (REU), May 26-Jul. 30, 2015, 1 page.
Wikipedia page for "Analyte" retrieved from "https://en.wikipedia.org/w/index.php?title=Analyte&oldid=527866671".
Wikipedia page for "Bluetooth Low Energy" retrieved from "https://en.wikipedia.org/w/index.php?title=Bluetooth_Low_Energy&oldid=744163272".
Wikipedia page for "Bluetooth" retrieved from "https://en.wikipedia.org/w/index.php?title=Bluetooth&oldid=744565671".
Wikipedia page for "Challenge-response authentication" retrieved from "https://en.wikipedia.org/w/index.php?title=Challenge-response_authentication&oldid=567947229".
Wikipedia page for "Digital signature" retrieved from "https://en.wikipedia.org/w/index.php?title=Digital_signature&oldid=523528508".
Wikipedia page for "In vivo" retrieved from https://en.wikipedia.org/w/index.php?title=In_vivo&oldid=524960105.

(56) References Cited

OTHER PUBLICATIONS

Wikipedia page for "Near-field communication" retrieved from "https://en.wikipedia.org/w/index.php?title=Near-field_communication&oldid=525308529".
Wikipedia page for "RSA (cryptosystem)" retrieved from "https://en.wikipedia.org/w/index.php?title=RSA_(cryptosystem)&oldid=582212268".
Wikipedia, The Free Encyclopedia, "Continuous glucose monitor", retrieved from https://en.wikipedia.org/w/index.php?title=Continuous_glucose_monitor&oldid=1180606331, 10 pages (Oct. 1, 2023).
Wikipedia, The Free Encyclopedia, "Radio-frequency identification", retrieved from https://en.wikipedia.org/wiki/Radio-frequency_identification, 30 pages (Oct. 23, 2023).
Wilson, G. S., et al., "Progress Toward the Development of an Implantable Sensor for Glucose", Clinical Chemistry, vol. 38, No. 9, 1992, pp. 1613-1617.
Youbok Lee, "RFID Coil Design", Microchip Technology Inc., DS00678B, pp. 1-19 (1998).
Zhang et al., "Bluetooth Low Energy for Wearable Sensor-based Healthcare Systems," 2014 Health Innovations and Point-of-Care Technologies Conferences, 4 pages (2014).
Custodio et al., "A Review on Architectures and Communications Technologies for Wearable Health-Monitoring Systems," Sensors 12:13907-13946 (2012).
Excerpts from the "German Health Report Diabetes 2023" of the German Diabetes Society, Nov. 14, 2022, 24 pgs. [with English translation].
Extract from the privacy notice for LibreView, Jul. 13, 2024, 7 pgs.
LibreLinkUp User Guide, Dec. 12, 2023, 28 pgs.
Morak et al., "Design and Evaluation of a Telemonitoring Concept Based on NFC-Enabled Mobile Phones and Sensor Devices," IEEE Transactions on Information Technology in Biomedicine, Nov. 2011, 8 pgs.
Mosa et al., "A Systemic Review of Healthcare Applications for Smartphones," BMC Medical Informatics and Decision Making 12:67 (2012) 32 pgs.
Padgette et al., "Guide to Bluetooth Security. Recommendations of the National Institute of Standards and Technology," NIST Special Publication 800-121, Revision 1, Jun. 2012, 47 pgs.
UPC Court of Appeal, Feb. 26, 2024, 335/2023, 38 pgs.
U.S. Appl. No. 17/113,560, filed Jan. 16, 2025 Non-Final Office Action.
U.S. Appl. No. 18/830,212, filed Dec. 6, 2024 Non-Final Office Action.
A Dictionary of Computer Science for "authentication", Seventh Edition, Oxford University Press, 3 pages (2016).
BBC News, Technology, Bluetooth rival unveiled by Nokia, 2 pgs. (Oct. 4, 2006).
Bloodborne pathogens, Occupational Safety and Health Admin., Labor, 29 CFR Ch. XVII (Jul. 1, 2003 Edition) § 1910.1030, pp. 260-273.
Bluetooth Specification V 2.1, Jul. 26, 2007, pp. 1-541.
Bluetooth Specification V 2.1, Jul. 26, 2007, pp. 542-906.
Burge, M, et al. "Continuous Glucose Monitoring: The Future of Diabetes Management", Diabetes Spectrum, vol. 21 (2), 2008, 9 pages.
Burr, et al., Electronic Authentication Guideline, NIST Special Publication 800-63-2, Computer Security, NIST National Institute of Standards and Technology, U.S. Department of Commerce, 123 pages (2013).
Dexcom STS 7 Plus User's Guide, 2011, 144 pgs.
Dexcom STS 7 User Guide, 2007, 74 pgs.
Diglas et al., "Reduced pain perception with Pen Mate™ an automatic needle insertion device for use with an insulin pen," Practical Diabetes Int 16(2):39-41 (1999).
Electronic Authentication Guide, 123 pgs. (Aug. 2013).
Expert Statement of Professor Pantelis Georgiou, Aug. 9, 2024, 52 pgs.
FreeStyle Libre Flash Glucose Monitoring System, User's Manual, Abbott Diabetes Care Ltd., 126 pages (2017).
FreeStyle Navigator Continuous Monitoring System, Summary of Safety and Effectiveness Data in support of Pre-Market Approval (PMA) No. P980022, Abbott Diabetes Care, 25 pages (1999).
Freestyle Navigator User Guide, 2008, 195 pgs.
Guardian Real Time User Guide, 2006, 181 pgs.
Hirsch, "Realistic Expectations and Practical Use of Continuous Glucose Monitoring for the Endocrinologist," J Clin Endocrinol Metab 94:2232-2238 (2009).
Hughes, "The Business of Self-Monitoring of Blood Glucose: A Market Profile," Journal of Diabetes Science and Technology, 3(5):1219-1223 (2009).
IEEE 100, The Authoritative Dictionary of IEEE Standards Terms for "authentication", Seventh Edition, Standards Information Network IEEE Press, 3 pages (2000).
In vitro diagnostic test systems—Requirements for blood-glucose monitoring systems for self-testing in managing diabetes mellitus, European Standard, ISO 15197, 44 pages, 2003.
Moore, "The Potential Use of Radio Frequency Identification Devices for Active Monitoring of Blood Glucose Levels," Journal of Diabetes Science and Technology 3(1):180-183 (2009).
Newton's Telecom Dictionary for "authenticate", 30th Updated, Expanded, Anniversary Edition, Harry Newton, 4 pages (2016).

ANALYTE MONITORING AND MANAGEMENT DEVICE AND METHOD TO ANALYZE THE FREQUENCY OF USER INTERACTION WITH THE DEVICE

RELATED APPLICATIONS

The present application is a continuation of U.S. patent application Ser. No. 18/183,773 filed Mar. 14, 2023, which is a continuation of U.S. patent application Ser. No. 17/531,271 filed Nov. 19, 2021, now U.S. Pat. No. 11,678,821, which is a continuation of U.S. patent application Ser. No. 17/113,560 filed Dec. 7, 2020, which is a continuation of U.S. patent application Ser. No. 15/916,255 filed Mar. 8, 2018, now U.S. Pat. No. 10,856,785, which is a continuation of U.S. patent application Ser. No. 14/629,447 filed Feb. 23, 2015, now U.S. Pat. No. 9,913,600, which is a continuation of U.S. patent application Ser. No. 13/448,287 filed Apr. 16, 2012, which is a continuation of U.S. patent application Ser. No. 12/147,464 filed Jun. 26, 2008, now U.S. Pat. No. 8,160,900, which claims priority under § 35 U.S.C. 119(c) to U.S. Provisional Application No. 60/947,026 filed Jun. 29, 2007 entitled "Analyte Monitoring and Management Device and Method to Analyze the Frequency of User Interaction with the Device," the disclosures of each of which are incorporated by reference for all purposes.

BACKGROUND

The detection of the level of analytes, such as glucose, lactate, oxygen, and the like, in certain individuals, is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using colormetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test.

In vivo glucose sensors that continuously or automatically monitor the individual's glucose level and enable individuals to more easily monitor their glucose, or other analyte levels are also commercially available. These systems may provide the user with accurate analyte levels at ten, five or even one minute intervals. Some examples of such systems are illustrated in U.S. Pat. No. 6,175,752, and in U.S. Patent Publication No. 2004/0186365 filed Dec. 26, 2003, now U.S. Pat. No. 7,811,231, entitled "Continuous Glucose Monitoring System and Methods of Use." Devices and systems for management of the analyte level may also be included in the analyte monitoring system. An example of an analyte management system is an insulin pump, which may manage the analyte level by, for example, delivering a dose of insulin to the user in response to the glucose levels of the user. The analyte management system may be automatic, user controlled, or any combination thereof.

Clinical studies have shown that some patients derive considerable benefits from an increased frequency of available analyte levels, a benefit provided by the analyte measuring systems. However, other patients derived little or no benefit from an increased availability of analyte levels. Using glucose monitoring as an example, patients who derived little or no value from the glucose monitoring systems were at an increased risk of hyperglycemic or hypoglycemic episodes.

Increasingly, research has associated the lack of frequent interaction with the analyte monitoring system as the reason that some patients potentially derive reduced value from the analyte monitoring systems. As a result, there is a need for a system which reminds or encourages the user to interact with the analyte monitoring system at a minimum frequency.

SUMMARY

Exemplary embodiments of the present disclosure overcome the above disadvantages and other disadvantages not described above and provide advantages which will be apparent from the following description of exemplary embodiments of the disclosure. Also, the present disclosure is not required to overcome the disadvantages described above.

According to one aspect of the present disclosure, there is provided methods to analyze user interaction with a medical device. Exemplary embodiments include methods to encourage user interaction with a medical device that may include monitoring a user's actual frequency of interaction with the medical device; comparing the user's actual frequency of interaction with the medical device to at least one predetermined target level of interaction; and alerting the user when the user's actual frequency of interaction with the medical device is equal to or below the at least one predetermined target level of interaction.

According to one aspect of the present disclosure, the user may be informed of the difference between the actual frequency of interaction with the medical device and the predetermined target level of interaction.

According to one aspect of the present disclosure the user may be alerted using an alarm. The alarm may be an audible and/or visual and/or vibrating alarm. According to another aspect of the present disclosure, the audible alarm may increase in loudness over time after being activated.

According to one aspect of the present disclosure the method may include a plurality of predetermined target levels of interaction, wherein alerting the user distinguishes between the plurality of target levels of interaction.

According to one aspect of the present disclosure, the user may be required to perform at least one step to turn off the alert. According to yet another aspect, the at least one step may be a decision related to the user's state of health.

According to one aspect of the present disclosure, the at least one predetermined target level of interaction may be adjusted by an authorized user. The at least one predetermined target level of interaction may also be adjusted according to a time of day, type of activity, or projected future analyte level.

According to another aspect of the present disclosure, the history of the user's actual frequency of interaction with the medical device may be recorded. In this aspect, the at least one predetermined target level of interaction may be adjusted according to the recorded history. Moreover, the history of the user's actual frequency of interaction with the medical device may be organized according to behavior variables inputted by the user. According to another aspect of the present disclosure, the at least one predetermined target level of interaction may be adjusted according to a data received from a sensor located on the user.

According to one aspect of the present disclosure, the user may be rewarded when the actual frequency of interaction stays above the at least one predetermined level of interaction for a predetermined time.

According to another aspect of the present disclosure, there is disclosed an analyte monitoring apparatus comprising a sensor which is attached to a user for monitoring an analyte level of the user, the sensor further comprising a transmitter which transmits information obtained by the sensor; and a receiver unit comprising a receiver for receiving data from the sensor, and a display coupled to the receiver which displays the received data to the user when the user interacts with the receiver unit, wherein the receiver unit monitors the user's actual frequency of interaction with the device, compares the user's actual frequency of interaction with the receiver unit to at least one predetermined target level of interaction, and alerts the user when the user's actual frequency of interaction with the receiver unit is equal to or below the at least one predetermined target level of interaction.

BRIEF DESCRIPTION OF THE DRAWINGS

The above and other features and advantages of the present disclosure will become more apparent from detailed exemplary embodiments set forth hereinafter with reference to the attached drawings in which.

DETAILED DESCRIPTION

Figure 1:
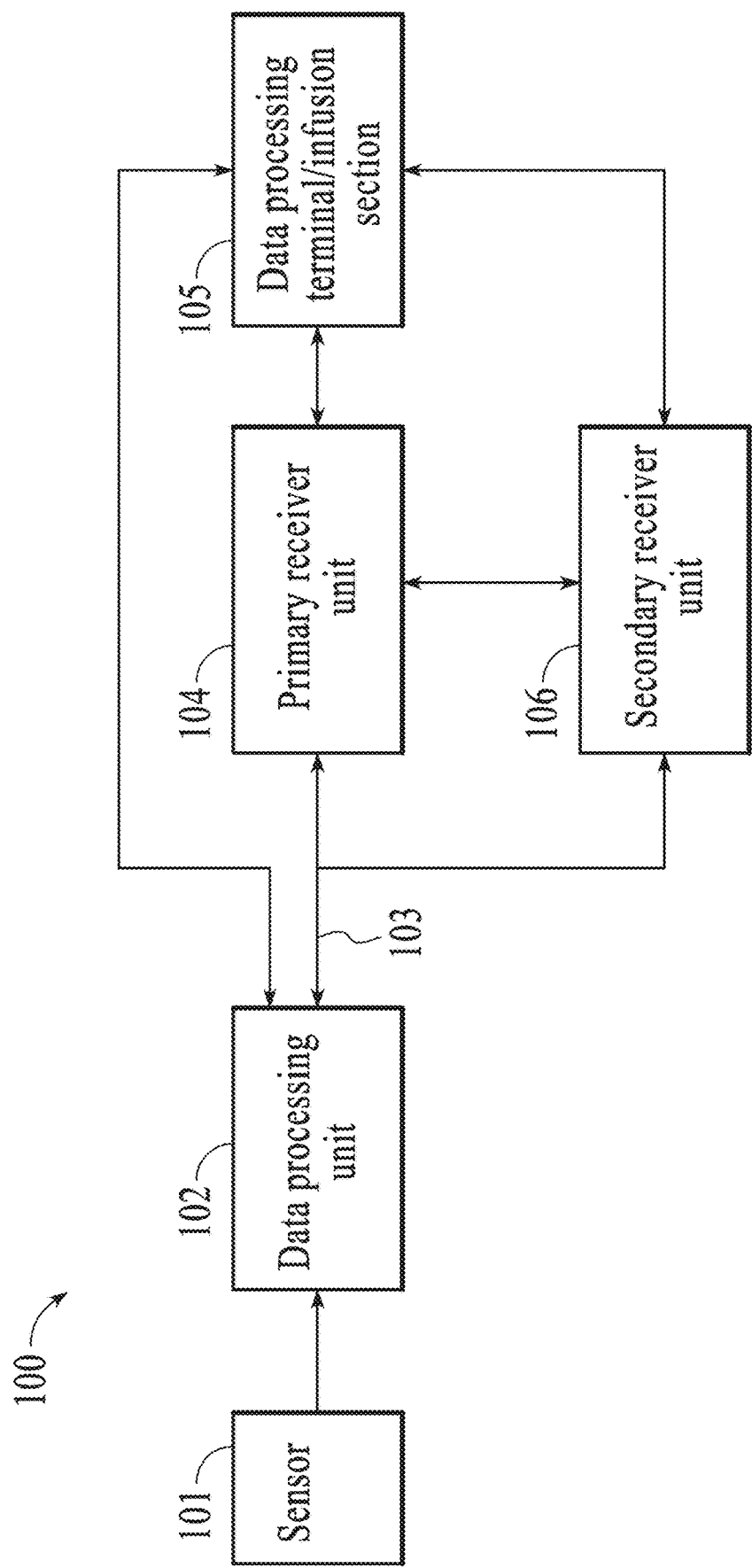
FIG. 1 is a block diagram of an exemplary embodiment of a data monitoring and management system according to the present disclosure.

The present disclosure will now be described more fully with reference to the accompanying figures, in which exemplary embodiments of the disclosure are shown. The figures shown herein are not necessarily drawn to scale, with some components and features being exaggerated for clarity. Like reference numerals in the figures denote like elements.

It is also to be understood that the terminology used herein is for the purpose of describing particular embodiments only, and is not intended to be limiting, since the scope of the present disclosure will be limited only by the appended claims. Unless defined otherwise, all technical and scientific terms used herein have the same meaning as commonly understood by one of ordinary skill in the art to which this disclosure belongs. It must be noted that as used herein and in the appended claims, the singular forms "a," "an," and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments are described herein generally with respect to in vivo analyte monitoring device and methods in which at least a portion of an analyte sensor is positioned beneath a skin surface of a user, where such description is not intended to limit the scope of the disclosure in any way. Also contemplated are in vitro analyte monitoring systems, e.g., small volume (e.g., sample volumes ranging from about 0.1 to about 1 microliter), and/or short assay times (e.g., assay times ranging from about 1 second to about 10 seconds). In vitro systems usually include a test strip and a meter to read the test strip. Examples of in vitro analyte systems include, but are not limited to, FreeStyle® and Precision® blood glucose monitoring systems from Abbott Diabetes Care Inc. Also contemplated are integrated systems in which one or more components of an in vitro system are included in a single housing, e.g., lance, test strip or meter.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Additionally, in one exemplary embodiment the analyte monitoring system may include an analyte management system, such as an insulin pump. Thus, it is to be understood that the following description is directed to an analyte (for example, glucose) monitoring system for convenience only and such description is in no way intended to limit the scope of the disclosure.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those exemplary embodiments that monitor more than one analyte, the analytes may be monitored at the same or different times.

Moreover, the description herein is directed primarily to electrochemical sensors for convenience only and is in no way intended to limit the scope of the disclosure. Other sensors and sensor systems are contemplated. Such include, but are not limited to, optical sensors, colorimetric sensors, and sensors that detect hydrogen peroxide to infer analyte levels, etc.

Referring to FIG. 1, the analyte monitoring system 100 includes a sensor 101, a data processing unit 102 connectable to the sensor 101, and a primary receiver unit 104, which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106. In one exemplary embodiment, the primary receiver unit 104 may be designed to sit on a shelf or nightstand. In this exemplary embodiment, the primary receiver unit 104 may be used by parents to monitor their children while they sleep or to awaken patients during the night. In addition, in this exemplary embodiment the primary receiver unit may include a lamp or a radio for convenience and/or for activation as an alarm.

Also shown in FIG. 1 is an optional secondary receiver unit 106 which is operatively coupled to the communication link and configured to communicate with the data processing unit 102. The secondary receiver unit 106 may also be configured to communicate with the primary receiver unit 104, as well as the data processing terminal 105. The secondary receiver unit 106 may be configured for bi-directional wireless communication with each of the data processing unit 102, the primary receiver unit 104 and the data processing terminal 105. In certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions) compact housing or be embodied in a device such as a wrist watch, arm band, etc., for example. Alternatively, the secondary receiver unit 106 may be configured with the same or substantially similar functions and features as the primary receiver unit 104. The secondary receiver unit 106 may also include a docking portion to be mated with a docking cradle unit for placement by, e.g., the bedside for night time monitoring, and/or a bi-directional communication device. A docking cradle may recharge a power supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101, and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor, or vice-versa.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 performs data processing functions, where such functions may include, but are not limited to, filtering and encoding of data signals, each of which corresponds to a sampled analyte level of the user, for transmission to a receiver unit (104 or 106) via the communication link 103. In certain embodiments, one or more application-specific integrated circuits (ASIC) may be used to implement one or more functions or routines associated with the operations of the data processing unit (and/or receiver unit) using for example one or more state machines and buffers.

In one embodiment, the sensor 101 or the data processing unit 102 or a combined sensor/data processing unit may be wholly implantable under the skin layer of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain exemplary embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), or a drug delivery device (e.g., an insulin pump), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

In certain embodiments, the communication link 103 as well as one or more of the other communication interfaces shown in FIG. 1, may use one or more of: a radio frequency (RF) communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
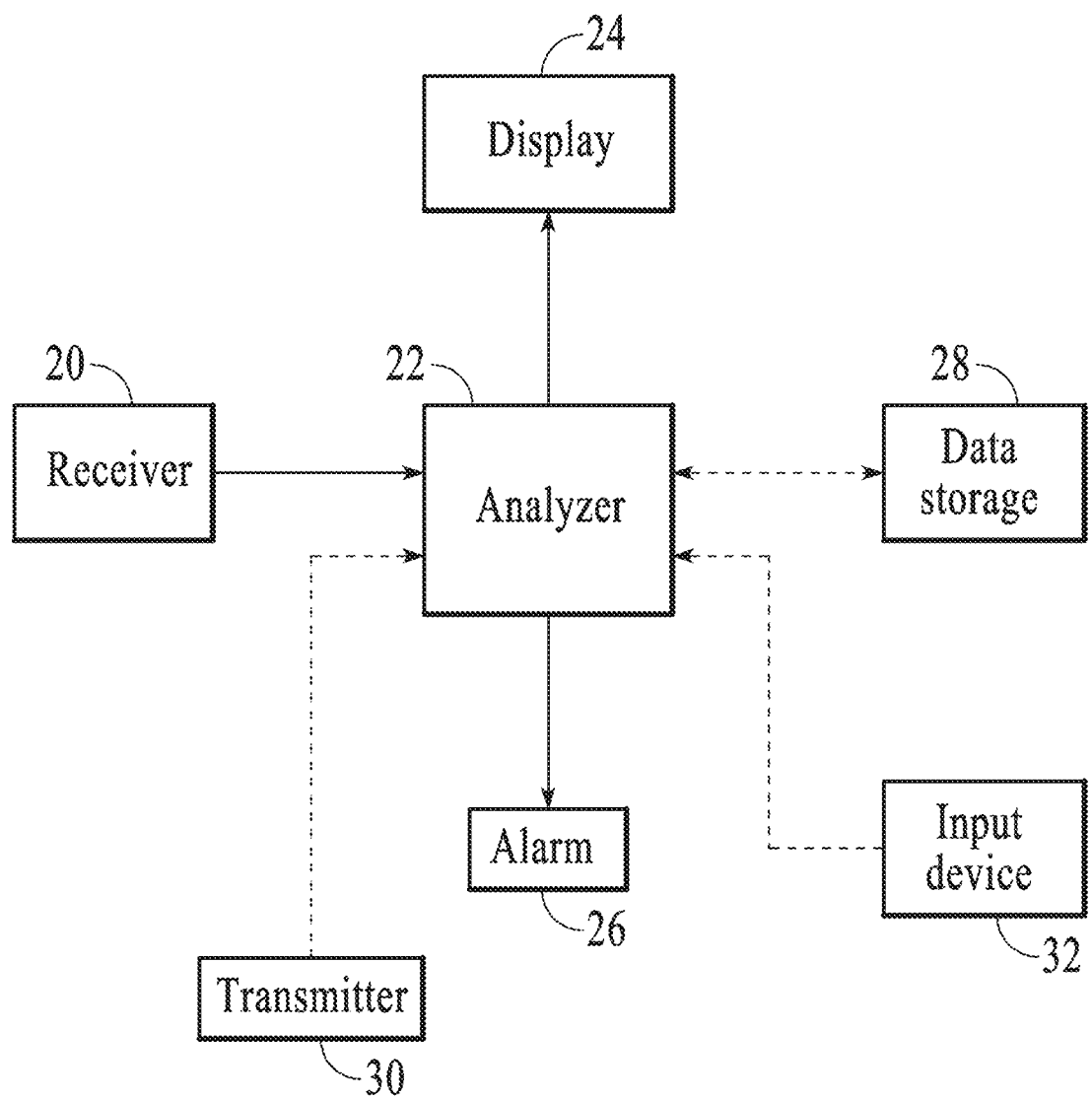
FIG. 2 is a block diagram of one exemplary embodiment of a receiver unit, according to the present disclosure.

The primary receiver unit 104, according to an exemplary embodiment of the present disclosure, illustrated in block form in FIG. 2, includes a receiver 20 to receive data from the data processing unit 102, an analyzer 22 to evaluate the data, a display 24 to provide information to the user, and an alarm system 26 to warn the user when a condition arises. The primary receiver unit 104 may also optionally include a data storage device 28, a transmitter 30, and/or an input device 32. As described above, the secondary receiver unit 106 may have the same structure as the primary receiver unit 104, and as such, the following description of receiver unit functions apply equally to the primary and secondary receiver units.

In one exemplary embodiment, a primary receiver unit 104 may be a bedside unit for use at home. The bedside unit may have its own data analyzer and data storage. The data may be communicated from the data processing unit 102 or another receiver unit, such as a secondary receiver unit 106. Thus, at least one receiver unit contains all the relevant data so that the data can be downloaded and analyzed without significant gaps.

The receiver 20 may be formed using known receiver and antenna circuitry and may be tuned or tunable to the frequency or frequency band of the data processing unit 102. In one exemplary embodiment, the receiver 20 is capable of receiving signals from a distance greater than the transmitting distance of the data processing unit 102.

In another embodiment, a repeater unit (not shown) is used to boost a signal from the data processing unit 102 so that the signal can be received by receiver units 104 and 106 that may be distant from the data processing unit 102. The repeater unit is typically independent of the data processing unit 102, but, in some cases, the repeater unit may be configured to attach to the data processing unit 102. Typically, the repeater unit includes a receiver for receiving the signals from the data processing unit 102 and a transmitter for transmitting the received signals. The transmitter of the repeater unit may be more powerful than the transmitter of the data processing unit 102 in one exemplary embodiment of the present disclosure. The repeater unit may be used, for example, in a child's bedroom for transmitting a signal from a data processing unit 102 on the child to a primary receiver unit 104 in the parent's bedroom for monitoring the child's analyte levels and frequency of interaction with the secondary receiver unit 106.

A variety of displays 24 may be used, including cathode ray tube displays (particularly for larger units), light emitting diode (LED) displays, or liquid crystal display (LCD) displays. The display 24 may be monochromatic (e.g., black and white) or polychromatic (i.e., having a range of colors). The display 24 may contain symbols or other indicators that are activated under certain conditions (e.g., an alert to the user may become visible on the display when the user's frequency of interaction with the receiver units 104 and 106 falls below the predetermined target level of interaction). The display 24 may also contain more complex structures, such as LCD or LED alphanumeric structures, portions of which can be activated to produce a letter, number, or symbol. For example, the display 24 may include region 34 to display numerically the level of the analyte, as illustrated in FIG. 3.

Figure 4:
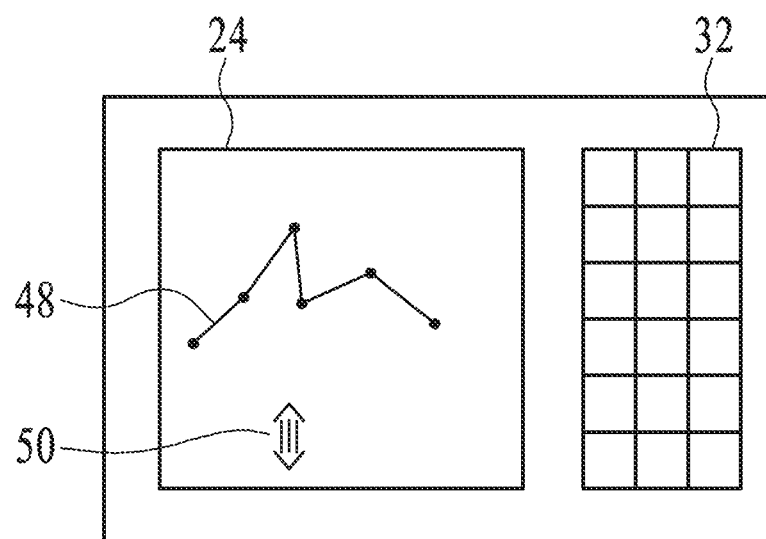
FIG. 4 is a front view of a second exemplary embodiment of a receiver unit.
Figure 5:
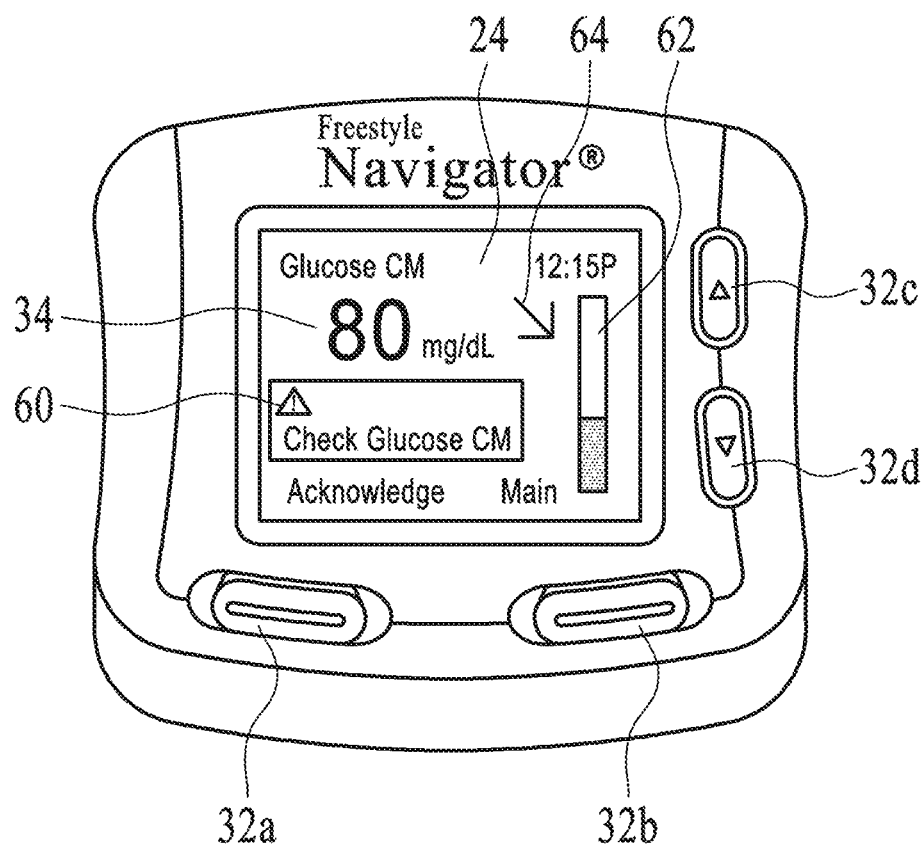
FIG. 5 is a front view of a third exemplary embodiment of a receiver unit.

In one exemplary embodiment, as shown in FIG. 5, the display 24 also provides a message 60 to the user to direct the user in an action. Such messages may include, for example, "Check Analyte Level", if the user's frequency of interaction with a receiver unit falls below the predetermined target level. In another exemplary embodiment, the messages may provide helpful hints or tips to the user. The display may also include other indicators 36, including directional arrows, etc., which may be activated under certain conditions. For example, indicator 38 of a glucose monitoring device, may be activated if the patient is hyperglycemic. Other indicators may be activated in the cases of hypoglycemia (40), impending hyperglycemia (42), impending hypoglycemia (44), a malfunction, an error condition, or when calibration of the device is required (46). In some embodiments, color coded indicators may be used. Alternatively, the portion 34 which displays the analyte concentration, may also include a composite indicator 50 (see FIG. 4), portions of which may be appropriately activated to indicate any of the conditions described above. In another exemplary embodiment, the display may be capable of displaying a graph 48 of the analyte level over a period of time, as illustrated in FIG. 4.

Figure 3:
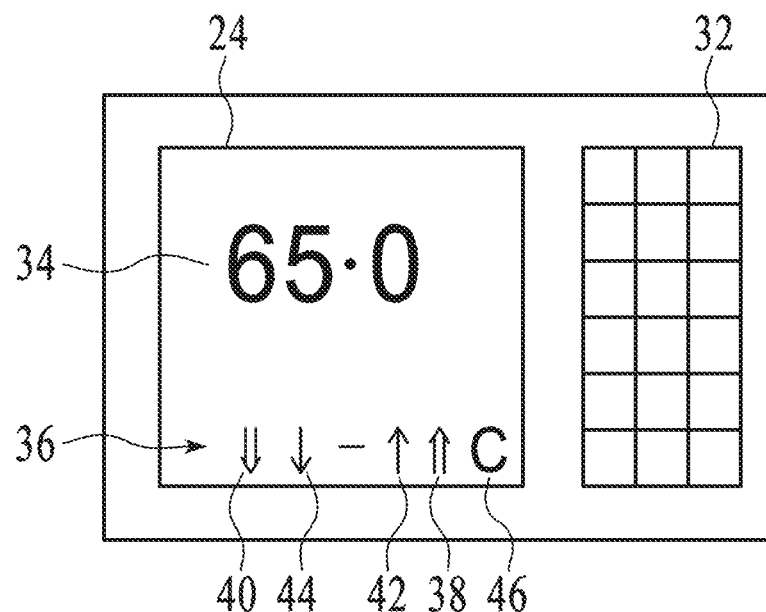
FIG. 3 is a front view of an exemplary embodiment of a receiver unit.

One example of a receiver unit (104 or 106) is illustrated in FIG. 3. The display 24 of this particular receiver unit (104 or 106) includes a portion 34 that displays the level of the analyte, for example, the blood glucose concentration. In one embodiment, the screen may be blank or dark when in the resting state. In this exemplary embodiment, the screen may be activated if the user interacts with the device. In another embodiment, the receiver unit (104 or 106) indicates the time of day on the default screen, and the user may view the current analyte level by interacting with the receiver unit (104 or 106), for example by pressing a button or the like on the receiver unit (104 or 106), which will display the current analyte level. In this way, receiver units 104 and 106 can monitor the frequency of interaction between the user and the receiver units 104 and 106.

In one exemplary embodiment, the user's interaction with the receiver units 104 and 106 is system specific. That is, the receiver units 104 and 106 update each other when the user interacts with one of the receiver units (either 104 or 106). In this embodiment, the user needs to only interact with one unit to maintain the target level of interaction.

In another embodiment, the user's interaction with the receiving units 104 and 106 may be receiver unit specific. One example where the user's interaction with the receiver is receiver unit specific may be a guardian/child relationship. In this example, the child's level of interaction (with, for example, the primary receiver unit 104) and the guardian's level of interaction (with, for example, the secondary receiver unit 106) should be assessed independently.

In another exemplary embodiment, as illustrated in FIG. 5, the display 24 may display a bar graph 62, or any other suitable indicator, comparing the user's frequency of interaction with the receiver units 104 and 106 to the predetermined target frequency. Additionally, as shown in FIG. 5, the display 24 may further be capable of displaying an analyte indicator 64, which may indicate the rate of change of the analyte, and the direction of change of the analyte, e.g., by the particular direction of an arrow or the like. In this exemplary embodiment, the analyte indicator 64 may point in different directions, such as for example, around a 360 degree Clock. Other examples of graphs may include graphs of the user's frequency of interaction with the receiver unit (104 or 106), or units (104 and 106), over a period of time, and graphs of the rate of change or acceleration in the rate of change of the analyte level over time.

In some exemplary embodiments, the receiver unit is configured so that the user may choose the particular display (e.g., blood glucose concentration or graph of concentration versus time) that the user wishes to view. The user may choose the desired display mode by pushing a button or the like, for example, on an optional input device 32. When the user interacts with the device, to view or choose a particular display or to wake the device from its resting state, the receiver unit 104 or 106 may record the date and time of the user's interaction with that receiver unit. In this way, the receiver units 104 and 106 can monitor the frequency of user interaction with the receiver units. The optional input device 32 for interacting with the receiver units 104 and 106 will be described in greater detail below.

The above-described graphs benefit both the user and the health care provider ("HCP"). The user can benefit from subtle behavioral modification as the graphs and/or screen prompts encourage more frequent interaction with the device and the expected improvement in outcomes.

HCPs may benefit from more cumulative statistics (such as average glucose views per day, average glucose views before/after meals, average glucose views on "in-control" vs. "out-of-control" days or time of day) which may be obtained from the record of user's interaction frequency with the device and which can be used to understand why a patient may not be realizing expected gains from the analyte monitoring system. If an HCP sees that a patient is not benefiting as expected from the analyte monitoring system, they may recommend an increased level of interaction (e.g., increase interaction target level).

In one exemplary embodiment, the receiver units 104 and 106 may include software. In this exemplary embodiment, each instance of user interaction, by pressing a button or the like, with a receiver unit 104 or 106, or both receiver units 104 and 106, may be recorded. The software may associate each instance of user interaction with the date and time of that interaction. For example, the software may record each instance that the user queries the main screen of the receiver unit 104 or 106. In this exemplary embodiment, the receiver unit 104 or 106 may further include an algorithm for comparing the frequency of user interaction with the receiver to a predetermined frequency of interaction. In this exemplary embodiment, if the frequency of a user's interaction with the receiver units 104 and 106 matches or falls below the predetermined level of interaction, the receiver unit (104 or 106) may alert the user through an audible or vibratory alert. The alert system will be described in greater detail below.

In another exemplary embodiment of the present disclosure, the receiver units 104 and 106 may also contain software designed to encourage interaction with the receiver units. For example, the software may set target rates for the user, so that the user strives to achieve a desired interaction frequency with the receiver unit. In another exemplary embodiment, the software may offer educational information related to treatment as well as helpful hints and tips, thereby educating the user as to the importance of maintaining a predetermined target level of interaction with the receiver unit.

In yet another embodiment, the receiver units 104 and 106 may include software that prompts user interaction, e.g., an electronic game, or cartoon-like character, or the like, that requires feedback from the user. In one exemplary embodiment, the cartoon-like character or the like may have a "health bar" or a "life bar" which would represent the level of interaction between the user and the analyte monitoring system 100. That is, by frequently interacting with the cartoon-like character, the user will keep the health, or life, level of the cartoon-like character above the predetermined target level. In one exemplary embodiment, the user may "feed" the cartoon-like character by interacting with the device. The user's analyte level, or other relevant information should also be displayed on the screen of the device during interaction between the user and the cartoon-like character. In one exemplary embodiment, the user will be limited in the amount of interaction in a predetermined time. That is, the user will not be able to front-load the amount of interaction with the device, and then ignore the device for a prolonged period of time. As such, the device may only record a predetermined number of interactions within a certain period of time.

By interacting with the cartoon-like character, the user may also be educated as to the benefits of maintaining a proper target rate of interaction with the device, or may at least stay informed as to his own state of health. This embodiment may be particularly interesting to children as it may help ensure that children maintain the necessary level of interaction with the monitoring device of this disclosure. This exemplary embodiment may also be coupled with education regarding treatment options, helpful hints and tips. Moreover, the above-described embodiment need not be used with a continuous glucose monitoring ("CGM") device.

In one exemplary embodiment of the present disclosure, the above concept can also be adapted to the "finger stick test." Using glucose as an example, the user may interact with the cartoon-like character by manually checking his blood glucose level. That is, each time the user manually checks his glucose level, using the finger stick test, the cartoon-like character may gain a point to the "health" or "life" bar. Similar to the embodiment described above, the "health" or "life" bar may represent the target level of user interaction. In this way, the user will desire to keep the cartoon-like character healthy, and thus interact with the device at an increased frequency. With regard to the embodiments described above, one of ordinary skill in the art will understand that the cartoon-like character is simply an example, and that any kind of character or figure may be used.

In order to achieve the full benefit of the analyte monitoring system 100, the user should maintain a predetermined target rate of interaction with the system. In one exemplary embodiment, the predetermined target level of user interaction is set by an HCP, or the user's health care team. Thus, each predetermined target level of interaction will likely depend on the specific user. However, in one exemplary embodiment, factors affecting the predetermined level of user interaction with the system may be: the particular analyte to be measured, the user's general state of health, (for example, more frequent during sick days), symptoms exhibited by the user, time of day, time since or until meal, activity level and other events.

In one exemplary embodiment, the target level may be programmed (or user modifiable) to vary during the course of the day or week (work week vs. weekend), with these rates being easily adjustable to account for events or changes, such as, during sick days, times of high activity, or other times when more frequent interactions should be encouraged. Although HCPs may recommend only general interaction levels (e.g., once per hour during waking hours), these levels may be tailored to the individual user. For example, if a user feels overwhelmed with CGM technology, lower target levels of interaction may be needed, whereas a user who feels empowered by the technology may be encouraged to interact with the device at a higher frequency. Generally, HCPs will review interaction levels during routine visits when assessing general health and reviewing data uploads (e.g., approximately every 3 months for patients with diabetes). However, this approach may differ depending on the user, or other factors.

In another exemplary embodiment, the predetermined target level of user interaction with the receiver units 104 and 106 may be set according to the time of day. For example, a user may interact with the receiver units 104 and 106 more frequently during the day than at night. Additionally, in another exemplary embodiment, the predetermined target level of user interaction with the receiver units 104 and 106 may be set according to the type of activity being performed by the user. For example, a user on a long-distance bicycle ride or car ride may need to check the analyte levels more frequently. In one exemplary embodiment, an HCP may recommend target levels of interaction corresponding to various events. In another exemplary embodiment, the target level of user interaction may be set by the user, or any other authorized party.

In one exemplary embodiment, the system may automatically adjust the target level of interaction based upon the user's activity level or state of general wellness. In this exemplary embodiment, the system may use pulse rate, body temperature, respiration rate or other indicators to adjust the analyte level. Alternatively, position sensors, accelerometers or the like may be used to detect sleep and reduce (or even suspend) the target interaction frequency.

In another exemplary embodiment, the analyte monitoring system 100 may use the detected analyte levels to adjust future target levels of interaction. For example, the system may use an increase in glucose level, an increase in the rate of change of the glucose level, user entered information or some other analysis of the measured analyte level to identify a need to adjust the current target level of interaction. In one exemplary embodiment, the analyte levels may detect that the user has recently had a meal and may then adjust the interaction frequency automatically to a pre-programmed or user-set level.

Another exemplary embodiment may include a plurality of predetermined target levels of user interaction with the system of the present disclosure. For example, the present disclosure may include an "ideal" level of interaction, an "acceptable" level of interaction and a "critical" level of interaction. These levels may shift based on several factors. In one exemplary embodiment, the level of interaction may be adjusted to an increased or decreased target level of interaction based upon the monitoring results, based upon some user interaction with the device (e.g., meal or activity level entry), or may be pre-programmed to vary with the time of day or day of the week. The monitoring results may include, analyte levels, the rate of change of analyte levels, etc.

In another exemplary embodiment, the interaction frequency level may be relative to the predetermined target interaction frequency. For example "ideal" may be approximately 90% or more of the target level; "acceptable" may be 70-90% of the target level; and "critical" may be below 70% of the target level.

In another exemplary embodiment of the present disclosure, the analyte monitoring system 100 may adjust the predetermined target levels of user interaction according to the condition of the user. Using glucose as an example, if the user's level of glucose drops below a certain threshold, the system may alert the user that hypoglycemia may occur. In this exemplary embodiment, the analyte monitoring system 100 may adjust the target rate of user interaction to be more frequent, thus prompting the user to interact with the device more often, and thus encourage the user to raise his level of glucose to a more acceptable level. Once the glucose level returns to an acceptable level, the system may adjust the target interaction rate accordingly.

In the above exemplary embodiment, the system may include a multiplier for adjusting target levels of user interaction, wherein the predetermined target rate of interaction is multiplied by a predetermined amount according to the condition reached. In one exemplary embodiment, a multiplier may be associated with a predetermined target level, such as for example the "critical" target level. In another exemplary embodiment, a multiplier may be associated with a specific condition, or analyte level of the user, such as when the user is in danger of becoming hypoglycemic.

In another exemplary embodiment, the system may adjust the rate of interaction according to predicted future analyte levels. For example, the analyte monitoring system 100 may predict the future analyte level of a user by monitoring the present rate of change of the user's analyte level.

As shown in FIG. 2, a receiver unit (104 or 106) may also optionally include an alarm system 26. In one exemplary embodiment, the alarm system 26 is triggered when the user's frequency of interaction with the receiver units 104 and 106 falls below a predetermined target level of interaction. In another exemplary embodiment, the alarm system 26 may be triggered when the user's level of interaction matches the predetermined target level of interaction.

The alarm system 26 may contain one or more individual alarms. Each of the alarms may be individually activated to indicate one or more predetermined target levels of user interaction with the receiver units 104 and 106. The alarms may be, for example, auditory or visual. Other sensory-stimulating alarm systems may be used, including alarm systems that direct the data processing unit 102 to heat, cool, vibrate, or produce a mild electrical shock. In some embodiments, the alarms are auditory with a different tone, note or volume indicating different predetermined target levels of user interaction with the receiver units 104 and 106. In one exemplary embodiment of the present disclosure, various tones of the alarm system 26 may indicate varying urgency levels of a user's need to interact with the receiver units 104 and 106. For example, a high volume alarm may indicate a "critical" predetermined target level being reached, while a lower volume alarm might indicate that the user's frequency of interaction has fallen below the "acceptable" level of interaction with the receiver unit. Visual alarms may also use a difference in color or brightness of the display, or indicators on the display, to distinguish between different predetermined target levels of user interaction with the receiver units 104 and 106. In some embodiments, an auditory alarm system may be configured so that the volume of the alarm increases over time until the alarm is deactivated.

In some embodiments, the alarms may be automatically deactivated after a predetermined time period. In other embodiments, the alarms may be configured to deactivate only when the user interacts with a receiver unit.

In another exemplary embodiment of the present disclosure, the receiver units 104 and 106 may include software for requiring the user to perform a series of operations in order to silence the alarm. In this exemplary embodiment, the operations may be therapeutic decision options being presented to the user, or may be a series of options related to the user's state of health. The user would then need to review these options and acknowledge understanding by interacting with the device. In certain cases, the alarm may not turn off unless the user acknowledges such understanding.

Figure 6:
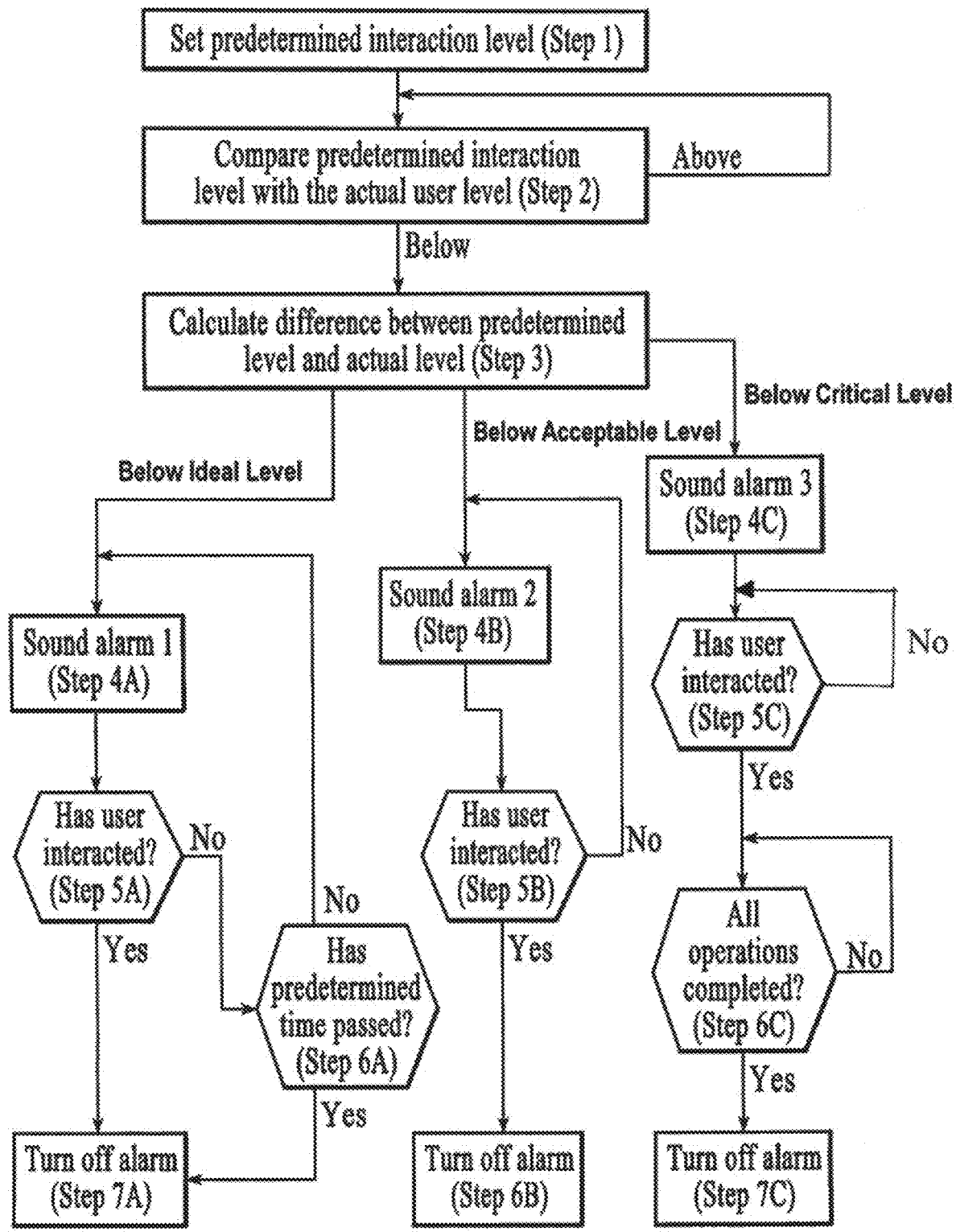
FIG. 6 is a chart of an analyte monitoring system according to an exemplary embodiment of the present disclosure.

FIG. 6 shows a chart according to an exemplary embodiment of the analyte monitoring system 100 of the present disclosure. As shown in Step 1 of FIG. 6, the predetermined target level of interaction is set. As discussed above, this level may be set by a user, an HCP, any other authorized person, or may automatically change depending on the factors discussed above. Next, in Step 2, the predetermined target level of user interaction is compared to the actual level of user interaction. If the user's actual level of interaction is above the predetermined target level, the system may simply wait. However, if the user's actual level of interaction falls below the target level, the system moves on to Step 3. In Step 3, the system calculates the difference between the actual level of user interaction and the predetermined target level.

In the exemplary embodiment shown in FIG. 6, there are three levels of user interaction, the "ideal," the "acceptable" and the "critical" level of interaction. In this exemplary embodiment, if the user's actual level of interaction falls below the "ideal" target level of user interaction, the user may be prompted to interact with the device (Step 4A). In one exemplary embodiment, the device will sound a low volume alarm for a predetermined period of time. That is, in Step 5A, the device will determine if the user has interacted with the device, and if the user has interacted, the alarm is turned off (Step 7A). As described above, the user may interact with the device by pressing a button or the like. If the user has not interacted with the device, the device determines whether a predetermined period of time has passed (Step 6A), and if it has, turns off the alarm.

Similarly, if the user's actual level of interaction falls below the "acceptable" target level of interaction, the system will prompt the user to interact with the device, by sounding an alarm or the like (Step 4B). In this example, as shown in Steps 5B and 6B, the alarm will not be turned off until the user has acknowledged the alarm, by pressing a button or the like.

If the user's actual level of interaction falls below the "critical" target level of interaction, the system will set off a third alarm (Step 4C). Similar to the "acceptable" target level, the alarm will not be turned off until the user has acknowledged the alarm (Step 5C). Additionally, to silence an alarm corresponding to the "critical" target level of interaction, the user may be required to perform a series of operations (Step 6C). Once the user completes the series of operations, the alarm is turned off (Step 7C).

One of ordinary skill in the art will understand that the analyte monitoring system of FIG. 6 is simply one possible example of the system according to the present disclosure. Steps other than those described in FIG. 6 may be included in the analyte monitoring system, and similarly, the system does not have to include all of the steps shown in FIG. 6. As such, FIG. 6 should not limit the present disclosure in any way, and is simply provided as one example of an analyte monitoring system according to an embodiment of the present disclosure.

As shown in FIG. 2, the receiver unit (104 or 106) may also include a transmitter 30 which can be used to transmit a signal to activate an alarm system (not shown) on the data processing unit 102. In one exemplary embodiment, the data processing unit 102 may include a receiver for communicating with the receiver units 104 or 106. In another exemplary embodiment, the data processing unit 102 may include an alarm system (not shown) such as the one included with the receiver units 104 and 106, wherein the alarm of the data processing unit 102 may be activated by a receiver unit (104 or 106).

A receiver unit (104 or 106) may also include a number of optional items. One such item may be, for example, a data storage unit 28. The data storage unit 28 may be used to store the history of user interaction with the receiver unit, among other data. The data storage unit 28 may also be useful to store data that may be downloaded to another receiver unit, such as the primary receiver unit 104. Alternatively, the data may be downloaded to a computer or other data storage device in a user's home, at an HCP's office, etc., for evaluation of trends in analyte levels.

In one exemplary embodiment, the HCP may use the recorded history of interaction to modify the treatment of the user. The storage unit 28 may also store behavior variables, such as events, together with the data of the particular event. These behavior variables may be generated either automatically by the receiver unit or can, alternatively, be input by the user. In an exemplary embodiment, the user may also edit the event history. Examples of events may include things such as the user's activity level, state of health, medication (e.g., insulin) dosages, meals or any other event that may have an effect on the assessment of a treatment approach and recommendations for treatment modifications of the user.

As shown in FIG. 2, another optional component for the receiver unit is an input device 32, such as a keypad or keyboard. The input device 32 may allow numeric or alphanumeric input. The input device 32 may also include buttons, keys, or the like which initiate functions of, and/or provide input to, the analyte monitoring system 100. Such functions may include interacting with a receiver unit, manually changing the target level of user interaction with the receiver unit, changing the settings of the receiver unit or entering behavior variables to be used together with the history of user interaction with the receiver unit, but are not limited to the above.

Referring to FIG. 5, there is provided an exemplary embodiment of a receiver unit. In FIG. 5, the user may interact with the receiver unit using input options 32a-d. In one exemplary embodiment, input options 32a and 32b are used to select the options shown on the display 24, while input options 32c and 32d are used to move through lists to highlight options and change settings. In another exemplary embodiment, a user's interaction with the integrated test strip, used to, for example, manually check the blood analyte level of a user, can be included as part of the user's interaction with the device.

In one exemplary embodiment, the user will have to acknowledge the alarm or message displayed by the receiver unit (104 or 106). In this exemplary embodiment, a receiver unit (104 or 106) may have a button which is the default button for acknowledging an alarm or message. However, some alarms may require the user to interact with a button other than the default button. Further, in certain exemplary embodiments, some alarms may require the user to perform a series of operations, such as pressing a combination of buttons or the like, in order to silence the alarm.

Another exemplary embodiment of the input device 32 is a touch screen display. The touch screen display may be incorporated into the display 24 or may be a separate display. The touch screen display is activated when the user touches the screen at a position indicated by a "soft button" which corresponds to a desired function.

In addition, the analyte monitoring system 100 may include password protection to prevent the unauthorized transmission of data to a terminal or the unauthorized changing of settings for the system 100. A user may be prompted by the receiver unit to input a password using the input device 32 whenever a password-protected function is initiated.

Accordingly, a method in one aspect includes monitoring a user's actual frequency of interaction with the medical device, comparing the user's actual frequency of interaction with the medical device to at least one predetermined target level of interaction, and alerting the user when the user's actual frequency of interaction with the medical device is equal to or below the at least one predetermined target level of interaction.

In one aspect, alerting the user may indicate a difference between the actual frequency of interaction with the medical device and the predetermined target level of interaction.

The user may be alerted by an audible alarm, where the audible alarm may increase in loudness over time after being activated.

In another aspect, the user may be alerted by a vibrating alarm.

The method in a further embodiment may include a plurality of predetermined target levels of interaction, where alerting the user distinguishes between the plurality of target levels of interaction.

The user may be required to perform at least one step to turn off the alert, where the at least one step may be a decision related to the user's state of health.

The at least one predetermined target level of interaction may be adjusted by an authorized user.

In a further aspect, the method may include adjusting the at least one predetermined target level of interaction according to a time of day.

The method may also include adjusting the at least one predetermined target level of interaction according to a type of activity.

Also, the method may still include adjusting the at least one predetermined target level of interaction according to a future analyte level of the user, predicted using rate of change data.

Additionally, the method may include recording a history of the user's actual frequency of interaction with the medical device, where the method may also include adjusting the at least one predetermined target level of interaction according to the recorded history.

In still yet a further embodiment, the method may include organizing the history of the user's actual frequency of interaction with the medical device according to behavior variables inputted by the user.

Further, the method may include rewarding the user when the actual frequency of interaction stays above the at least one predetermined level of interaction for a predetermined time.

Additionally, the method may include adjusting the at least one predetermined target level of interaction according to a data received from a sensor located on the user.

An analyte monitoring system in accordance with another embodiment includes a user interactive analyte device to monitor at least one analyte of a user, and a processor unit coupled to the user interactive device to determine the frequency of user interaction with the analyte monitoring device.

The analyte may include glucose.

In still yet a further aspect, the user interactive device may include an in vivo analyte sensor, where the sensor may be configured to at least be partially positioned under a skin surface of a user.

An analyte monitoring system in accordance with still another embodiment may include a sensor to monitor an analyte level of the user, a transmitter to transmit information obtained by the sensor, and a receiver unit comprising a receiver to receive data from the sensor, and a display coupled to the receiver to display the received data to the user when the user interacts with the receiver unit, where the receiver unit monitors the user's actual frequency of interaction with the device, compares the user's actual frequency of interaction with the receiver unit to at least one predetermined target level of interaction, and alerts the user when the user's actual frequency of interaction with the receiver unit is equal to or below the at least one predetermined target level of interaction.

The system in one aspect may include a data storage unit for storing a history of the user's actual interaction with the receiver unit.

The receiver unit may be portable.

The receiver unit may include a user input unit for interacting with the display unit.

Further, the user input unit may be used to change settings of the receiver unit.

Although the exemplary embodiment of the present disclosure have been described, it will be understood by those skilled in the art that the present disclosure should not be limited to the described exemplary embodiments, but various changes and modifications can be made within the spirit and the scope of the present disclosure. Accordingly, the scope of the present disclosure is not limited to the described range of the following claims.

What is claimed is:

1. A method comprising:
    establishing, using a software executed on a reader, a wireless communication channel using Bluetooth enabled communication protocol with a data processing unit, wherein the data processing unit is connected to a glucose sensor, wherein the glucose sensor is in contact with a bodily fluid under a skin surface of a user and configured to sense glucose levels in the bodily fluid;
    after the wireless communication channel is established, periodically receiving, by a wristwatch, glucose level information from the data processing unit via the wireless communication channel, wherein the glucose level information is generated by the data processing unit based on glucose levels sensed by the glucose sensor, wherein the wristwatch comprises a display and a user input device, wherein the wristwatch comprises a resting state and an active state, the active state including at least a first display mode and a second display mode;
    receiving, via the user input device of the wristwatch, a selection of the first display mode or the second display mode, wherein the first display mode is configured to display a current glucose level based on the received glucose level information and the second display mode is configured to display a graph of the received glucose level information over a period of time; and
    in response to a determination that the wristwatch is in the active state, displaying at least one of the current glucose level and the graph of the received glucose level information on the display in the selected display mode.

2. The method of claim 1, wherein the wristwatch receives glucose level information from the data processing unit every 5 minutes.

3. The method of claim 1, wherein at least one of the first display mode and the second display mode comprises an arrow indicating a direction of a change of the sensed glucose level.

4. The method of claim 1, wherein at least one of the first display mode and the second display mode comprise displaying the time of day.

5. The method of claim 1, wherein at least one of the first display mode and the second display mode comprises a color-coded indicator.

6. The method of claim 1, further comprising generating an alarm when a condition arises, wherein the alarm comprises an auditory alarm.

7. The method of claim 1, further comprising generating an alarm when a condition arises, wherein the alarm comprises a vibratory alarm.

8. The method of claim 1, further comprising generating an alarm when a condition arises, wherein the alarm comprises a visual alarm.

9. The method of claim 1, further comprising receiving an input via the user input device of the wristwatch such that the wristwatch transitions from the resting state to the active state.

10. The method of claim 1, wherein the wireless communication channel is established using a unique identifier of the data processing unit.

11. A method for displaying glucose level information on a wristwatch worn by a user, the glucose level information generated by a data processing unit connected to a glucose sensor in contact with a bodily fluid under a skin surface of the user, the glucose sensor configured to sense glucose levels in the bodily fluid and the data processing unit configured to generate the glucose level information based on the sensed glucose levels, the method comprising:
  establishing, using a software executed on a reader, a wireless communication channel using Bluetooth enabled communication protocol with a data processing unit;
  after the wireless communication channel is established, periodically receiving over a period of time, by the wristwatch, the glucose level information from the data processing unit, wherein the wristwatch comprises a display and a user input device, wherein the wristwatch comprises a resting state and an active state, the active state including at least a first display mode and a second display mode;
  receiving, via the user input device of the wristwatch, a selection of the first display mode or the second display mode, wherein the first display mode is configured to display a current glucose level based on the received glucose level information and the second display mode is configured to display a graph of the received glucose level information over a period of time; and
  in response to a determination that the wristwatch is in the active state, displaying at least one of the current glucose level and the graph of the received glucose level information on the display in the selected display mode.

12. The method of claim 11, wherein the wristwatch receives glucose level information from the data processing unit every 5 minutes.

13. The method of claim 11, wherein at least one of the first display mode and the second display mode comprises an arrow indicating a direction of a change of the sensed glucose level.

14. The method of claim 11, wherein at least one of the first display mode and the second display mode comprise displaying the time of day.

15. The method of claim 11, wherein at least one of the first display mode and the second display mode comprises a color-coded indicator.

16. The method of claim 11, further comprising generating an alarm when a condition arises, wherein the alarm comprises an auditory alarm.

17. The method of claim 11, further comprising generating an alarm when a condition arises, wherein the alarm comprises a vibratory alarm.

18. The method of claim 11, further comprising generating an alarm when a condition arises, wherein the alarm comprises a visual alarm.

19. The method of claim 11, further comprising receiving an input via the user input device of the wristwatch such that the wristwatch transitions from the resting state to the active state.

20. The method of claim 11, wherein the wireless communication channel is established using a unique identifier of the data processing unit.

21. A method comprising:
  periodically receiving, by a wristwatch from a data processing unit via a wireless communication channel using Bluetooth enabled communication protocol, glucose level information generated by the data processing unit based on glucose levels sensed by a glucose sensor, wherein the data processing unit is connected to the glucose sensor, wherein the glucose sensor is in contact with a bodily fluid under a skin surface of a user and configured to sense glucose levels in the bodily fluid, wherein the wristwatch comprises a display and a user input device, wherein the wristwatch comprises a resting state and an active state, the active state including at least a first display mode and a second display mode;
  receiving, via the user input device of the wristwatch, a selection of the first display mode or the second display mode, wherein the first display mode is configured to display a current glucose level based on the received glucose level information and the second display mode is configured to display a graph of the received glucose level information over a period of time; and
  in response to a determination that the wristwatch is in the active state, displaying at least one of the current glucose level and the graph of the received glucose level information on the display in the selected display mode.

22. The method of claim 21, wherein the wristwatch receives glucose level information from the data processing unit every 5 minutes.

23. The method of claim 21, wherein at least one of the first display mode and the second display mode comprises an arrow indicating a direction of a change of the sensed glucose level.

24. The method of claim 21, wherein at least one of the first display mode and the second display mode comprise displaying the time of day.

25. The method of claim 21, wherein at least one of the first display mode and the second display mode comprises a color-coded indicator.

26. The method of claim 21, further comprising generating an alarm when a condition arises, wherein the alarm comprises an auditory alarm.

27. The method of claim 21, further comprising generating an alarm when a condition arises, wherein the alarm comprises a vibratory alarm.

28. The method of claim 21, further comprising generating an alarm when a condition arises, wherein the alarm comprises a visual alarm.

29. The method of claim 21, further comprising receiving an input via the user input device of the wristwatch such that the wristwatch transitions from the resting state to the active state.

30. The method of claim 21, wherein the wireless communication channel is established using a unique identifier of the data processing unit.

* * * * *